United States Patent
Ito et al.

(10) Patent No.: US 11,697,643 B2
(45) Date of Patent: Jul. 11, 2023

(54) USE OF FUNCTIONALIZED ALPHA-ANGELICA LACTONES

(71) Applicant: Henkel AG & Co. KGaA, Duesseldorf (DE)

(72) Inventors: Kenji Ito, Duesseldorf (DE); Andreas Taden, Duesseldorf (DE)

(73) Assignee: Henkel AG & Co. KGaA, Duesseldorf (DE)

( * ) Notice: Subject to any disclaimer, the term of this patent is extended or adjusted under 35 U.S.C. 154(b) by 0 days.

(21) Appl. No.: 17/451,165

(22) Filed: Oct. 18, 2021

(65) Prior Publication Data

US 2022/0106280 A1    Apr. 7, 2022

Related U.S. Application Data

(63) Continuation of application No. PCT/EP2020/059347, filed on Apr. 2, 2020.

(30) Foreign Application Priority Data

Apr. 16, 2019    (EP) ..................... 19169509

(51) Int. Cl.
| | |
|---|---|
| *C08G 59/40* | (2006.01) |
| *C08G 59/56* | (2006.01) |
| *C08G 59/66* | (2006.01) |
| *C08L 63/00* | (2006.01) |
| *C07D 307/58* | (2006.01) |
| *C08G 59/06* | (2006.01) |
| *C08G 59/14* | (2006.01) |
| *C08G 59/50* | (2006.01) |
| *C08G 59/62* | (2006.01) |

(52) U.S. Cl.
CPC ......... *C07D 307/58* (2013.01); *C08G 59/063* (2013.01); *C08G 59/1438* (2013.01); *C08G 59/502* (2013.01); *C08G 59/56* (2013.01); *C08G 59/626* (2013.01); *C08G 59/66* (2013.01)

(58) Field of Classification Search
None
See application file for complete search history.

(56) References Cited

U.S. PATENT DOCUMENTS

| | | |
|---|---|---|
| 3,113,708 A | 12/1963 | Moulic, Jr. |
| 3,535,342 A | 10/1970 | Emmons |
| 4,069,055 A | 1/1978 | Crivello |
| 4,216,288 A | 8/1980 | Crivello |
| 4,250,311 A | 2/1981 | Crivello |
| 4,835,289 A | 5/1989 | Brindoepke |
| 4,892,954 A | 1/1990 | Brindeopke et al. |
| 5,084,586 A | 1/1992 | Farooq |
| 5,124,417 A | 6/1992 | Farooq |
| 5,554,664 A | 9/1996 | Lamanna et al. |
| 6,129,244 A | 10/2000 | Hoerth |
| 8,313,006 B2 | 11/2012 | Willner et al. |
| 2012/0148740 A1 | 6/2012 | Yang et al. |
| 2013/0261254 A1* | 10/2013 | Mullen ............... C08L 63/10 525/445 |
| 2017/0009005 A1 | 1/2017 | Urban et al. |

FOREIGN PATENT DOCUMENTS

| | | | |
|---|---|---|---|
| CN | 101348558 | 1/2009 | |
| EP | 0119840 | 9/1984 | |
| GB | 1485925 | 9/1977 | |
| JP | 53025553 A * | 3/1978 | .......... C07D 307/46 |
| JP | 2006028528 | 2/2006 | |
| WO | 2019040389 | 2/2019 | |

OTHER PUBLICATIONS

Machine translation of JP-53025553-A (no date).*
Brügel, W., Dury, K., Stengel, G. and Suter, H. (1956), Zur Carbonyl-Frequenz substituierter ungesättigter 5-Ringlactone. Angewandte Chemie, 68: 440-440. https://doi.org/10.1002/ange.19560681309 (Year: 1956).*
Asaoka, MorioChemistry. "New Synthetic Method of 5- and 2,5-Substituted 3-Furoates, and 1,4-Dicarbonyl Compounds from Unsaturated Lactones." Chemistry letters. 2 (1977): 171-174. Web. (Year: 1977).*
PCT International Search Report—WO PCT/EP2020/059347—dated Jun. 4, 2020.

* cited by examiner

*Primary Examiner* — Michael J Feely
(74) *Attorney, Agent, or Firm* — Steven C. Bauman

(57) ABSTRACT

The present invention is directed to the use as a reactive component in the curing of compositions based on epoxy resins of a functionalized α-angelica lactone (XOMAL) having the general formula:

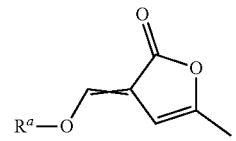

wherein: $R^a$ is a $C_1$-$C_{30}$ alkyl, $C_3$-$C_{30}$ cycloalkyl, $C_6$-$C_{18}$ aryl or $C_2$-$C_{12}$ alkenyl group.

14 Claims, 1 Drawing Sheet

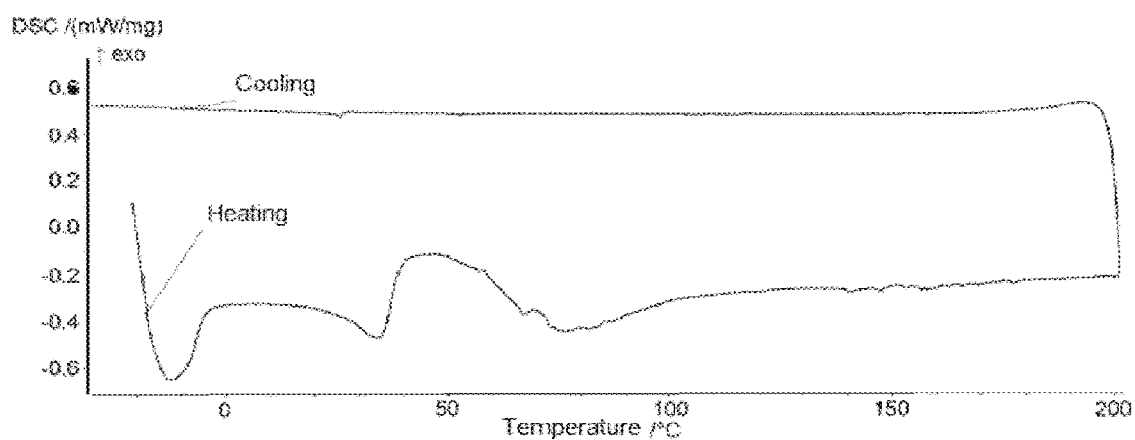

USE OF FUNCTIONALIZED ALPHA-ANGELICA LACTONES

FIELD OF THE INVENTION

The present invention is directed to curable compositions which may be obtained using renewable feedstock. More particularly, the present invention is directed to curable compositions based on epoxy resins and which comprise at least one reactant derivable from a renewable feedstock, the incorporation of which reactant(s) into the cured composition renders that product bio-renewable.

BACKGROUND OF THE INVENTION

Epoxy resins are reactive intermediates used to produce a versatile class of thermosetting polymers: these resins are ubiquitous components in coating, adhesive and sealant compositions, in composite materials and in structural applications on account of: their mechanical properties, such as toughness; their chemical properties, including their adhesion and chemical (corrosion) resistance; and, their electrical and heat resistance.

Epoxy resins are characterized by the presence of a three-membered cyclic ether group commonly referred to as an epoxy group, 1,2-epoxide or oxirane. These resins are traditionally derived from petroleum, the processing of which resource has a number of associated harmful environmental impacts. Moreover, a number of negative health impacts associated with residual monomeric epoxide compounds in polymers and with epoxy resins derived from bisphenol A in themselves have been investigated: in the latter regard, instructive literature includes Vandenberg et al. *Human exposure to bisphenol A (BPA)* Reproductive Toxicology, Issue 24(2):139-77 (2007) and Gupta et al. *Genetic Mouse Models for Female Reproductive Toxicology Studies* Comprehensive Toxicology (Second Edition), Volume 11 (2010), Pages 561-575.

On account of these disadvantages, some attention in the art has been directed to investigating the modification of traditional epoxy resin components with sustainable materials.

Czub *Application of Modified Natural Oils as Reactive Diluents for Epoxy Resins* Volume 242, Issue 1, Special Issue of the 14$^{th}$ Annual Polychar World Forum on Advanced Materials (2006) describes a bisphenol A based low-molecular-weight epoxy resin which has been modified with epoxidized soybean oil. Similarly, Jin et al. *Impact-strength improvement of epoxy resins reinforced with a biodegradable polymer* Polymer International 2008a, 57 (4), 577-583 describes bio-based epoxy materials which have been prepared from diglycidylether of bisphenol-A (DGEBA) and epoxidized soybean oil (ESO) with a thermally latent initiator. And likewise, Miyagawa et al. *Fracture toughness and impact strength of anhydride-cured biobased epoxy* Polym. Eng. Sci. 2005, 45 (4), 487-495 describes bio-based, neat epoxy materials containing functionalized vegetable oils (FVO), such as epoxidized linseed oil (ELO) and epoxidized soybean oil (ESO) which have been processed with an anhydride curing agent. It is noted that the vegetable oil-containing epoxy resins of these citations exhibit a high fracture toughness and impact strength but a concomitant decrease in glass transition temperature ($T_g$) on account of a decrease in the crosslink density and increase in chain flexibility.

Other raw material sources have also been considered for the development of epoxy resins. In Busto et al. *Controlling Water Uptake of Sugar Based Epoxy Resins* IEEE, New York (2011), isosorbide—a glucose-derived molecule—was incorporated into epoxy resins: isosorbide has a rigid structure and possesses hydroxyl groups which are amendable to conversion to epoxide groups as required for polymer growth. van Beilen and Poirier, Plant Journal 2008, 54 (4), 684-701 describe the functionalization of furans—which are derivable from plant sugars and polysaccharides—with carboxylic acids and the subsequent conversion of said functionalized compounds to epoxides or amines. Still further, rosins obtained from sources such as pines and other conifers (Liu, et al., Express Polymer Letters 2012, 6 (4), Pages 293-298), lignin (Simionescu et al. Composites Science and Technology 1993, 48, Pages 317-323) and cellulose (Varma and Chavan, Cellulose 1994, 1, 215-219) have each been used to synthesize epoxy resin components.

Unfortunately, the resulting resins of these citations were not shown to exhibit all of the physical properties required of this class of material to compete with traditional epoxy resins. Furthermore, complex and multi-step syntheses were often required to produce the resin precursors. With regard to lignin for example, the complexity of preparing lignin derivatives to act either as co-monomers with epoxide compounds or as curing agents for said epoxide compounds is documented in inter alia US20120148740A1, CN 101348558 B1 and JP2006/028528 A1.

Aside from the acknowledged need to incorporate sustainably-sourced compounds into epoxy resin materials, it would be advantageous to develop such materials which could be recycled. Unfortunately, the degradation of cured epoxy resin is stymied by the mechanical properties and chemical resistance of that resin. And there are "knock-on" effects of this. For example, composite materials such as carbon fiber reinforced plastics have been commonly prepared by using epoxy resins and are widely used to the reduce weight of structural assemblies: however, most of these assemblies have to be disposed of after their usage, in spite of the fact that carbon fiber is relatively expensive material.

On the basis of the above, there is considered to be an evident need to in the art to develop resins which are based on epoxide compounds and further sustainably sourced compounds but of which the mechanical and chemical properties have not been compromised by the inclusion of the latter compounds. Moreover, there is a further need to develop cured epoxy resins which can be degraded under sufficiently mild conditions to enable their facile recycling.

BRIEF DESCRIPTION OF THE DRAWINGS

FIG. 1 appended hereto illustrates the results of a Differential Scanning calorimetry (DSC) analysis of a composition in accordance with an embodiment of the present invention.

STATEMENT OF THE INVENTION

In accordance with a first aspect of the present invention, there is provided the use as a reactive component in the curing of compositions based on epoxy resins of a functionalized α-angelica lactone (XOMAL) having the general formula:

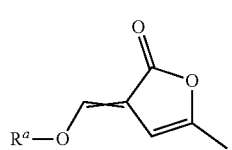

wherein: $R^a$ is a $C_1$-$C_{30}$ alkyl, $C_3$-$C_{30}$ cycloalkyl, $C_6$-$C_{18}$ aryl or $C_2$-$C_{12}$ alkenyl group.

The

notation is used herein to indicate that all stereoisomers fall within the scope of this general formula (XOMAL). Said functionalized α-angelica lactone (XOMAL)—as used as a reactive component—may therefore have the following structure:

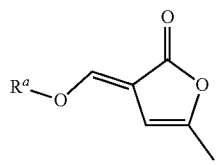 or 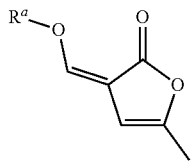

wherein, for instance, substituent $R^a$ of both said stereoisomers may be a $C_1$-$C_{18}$ alkyl, $C_3$-$C_{18}$ cycloalkyl, $C_6$-$C_{18}$ aryl or $C_2$-$C_{10}$ alkenyl group.

In an important embodiment of the functionalized α-angelica lactone (XOMAL), $R^a$ is a $C_1$-$C_{12}$ alkyl or $C_2$-$C_8$ alkenyl group, in particular a $C_1$-$C_6$ alkyl or $C_2$-$C_4$ alkenyl group. In a further embodiment, which is not intended to be mutually exclusive of that described above, said functionalized α-angelica lactone (XOMAL) is characterized in that $R^a$ is a $C_1$-$C_4$ alkyl or $C_2$-$C_4$ alkenyl group. A particular preference may be noted for the use as a reactive component of the compound:

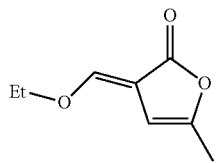

The conventional α-angelica lactone source material for the functionalized α-angelica lactone (XOMAL) is itself a derivative of Levulinic acid (LA), the latter compound being obtainable from renewable resources as recognized in Bozell et al. *Technology Development for the Production of Biobased Products from Biorefinery Carbohydrides—the US Department of Energy's "Top 10" revisited*, Green Chem. 2010, 12, 539-554. Moreover, the renewable sourcing of α-angelica lactone is discussed in Lima et al. *Angelica Lactones: from Biomass-Derived Plat-form Chemicals to Value-Added Products*, ChemSusChem 2018, 11, 25-47.

In accordance with a second aspect of the invention, there is provided a reactive composition comprising:
  a) a functionalized α-angelica lactone (XOMAL) as described hereinabove having the general formula

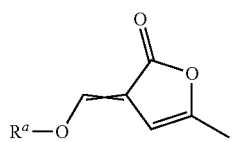

wherein $R^a$ is a $C_1$-$C_{30}$ alkyl, $C_3$-$C_{30}$ cycloalkyl, $C_6$-$C_{18}$ aryl or $C_2$-$C_{12}$ alkenyl group; and
  b) either one or both of:
    i) at least one polyamine having at least two amine hydrogens reactive toward epoxide groups; and,
    ii) at least one mercapto compound having at least two mercapto groups reactive toward epoxide groups.

This aspect of the invention provides for the preparation of reactive compositions based on the XOMAL compound—advantageously derivable from renewable resources—and two common hardeners used in the curing of epoxy resins.

Where the reactive composition is based on b) ii) at least one mercapto compound, a catalytic amount of a suitable compound should be included to initiate the actual reaction between parts a) and b). In particular, the present invention provides for the presence of a tertiary amine catalyst in the composition which functions by de-protonation of thiol (—SH) groups present to reactive the thiolate (—S$^-$) moiety.

In accordance with a third aspect of the present invention, there is provided a curable composition comprising:
  a) a functionalized α-angelica lactone (XOMAL) having the general formula

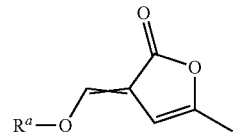

wherein $R^a$ is a $C_1$-$C_{30}$ alkyl, $C_3$-$C_{30}$ cycloalkyl, $C_6$-$C_{18}$ aryl or $C_2$-$C_{12}$ alkenyl group;
  b) either one or both of:
    i) at least one polyamine having at least two amine hydrogens reactive toward epoxide groups; and,
    ii) at least one mercapto compound having at least two mercapto groups reactive toward epoxide groups; and,
  c) at least one epoxide compound.

In an embodiment of this aspect of the invention, the curable composition should comprise, based on the weight of the composition:
  from 1 to 70 wt. % a) a functionalized α-angelica lactone (XOMAL) having the general formula:

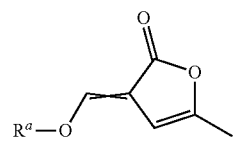

wherein $R^a$ is a $C_1$-$C_{30}$ alkyl, $C_3$-$C_{30}$ cycloalkyl, $C_6$-$C_{18}$ aryl or $C_2$-$C_{12}$ alkenyl group.
  from 30 to 70 wt. % of b) a curative component, said component comprising:
    i) at least one polyamine having at least two amine hydrogens reactive toward epoxide groups; and/or
    ii) at least one mercapto compound having at least two mercapto groups reactive toward epoxide groups; and, from 10 to 80 wt. % of c) at least one epoxide compound.

The curable composition should desirably be characterized by a molar ratio of epoxy-reactive groups to epoxy groups from 0.95:1 to 1.5:1, more preferably from 0.95:1 to 1.1:1. The curable composition should desirably be characterized in that said at least one epoxide compound is a polyepoxide selected from the group consisting of: glycidyl ethers of polyhydric alcohols and polyhydric phenols; glycidyl esters of polycarboxylic acids; and epoxidized polyethylenically unsaturated esters, ethers and amides.

This third aspect of the present invention provides for a curable composition based on bio-renewable XOMAL, epoxy resins and the curative compounds for said epoxy resins. The curable compositions may be prepared as one (1K) or two (2K) component compositions and find utility in coating, adhesive and sealant applications. The percentage by weight of XOMAL included in the curable composition is evidently determinative of the renewable content of that composition, which content can be further enhanced in certain circumstances by the selection of renewable curative compounds such as renewably sourced polyamines.

In accordance with a final aspect of the present invention, there is provided a cured product obtained from the curable composition as defined hereinabove and in the appended claims. Advantageously, the cured resin is degradable by acid-catalyzed hydrolysis, thereby enabling adhesives, sealants, coatings and other structures based on the thermoset resins to be debonded or disassembled for recycling purposes.

Without wishing to be bound by theory, the cured reaction product will contain aminoacetal (aminal) or thioacetal groups which constitute degradable moieties. As discussed in Chao et al. *Investigation of Secondary Amine-Derived Aminal Bond Exchange toward the Development of Covalent Adaptable Networks*, Macromolecules 2019 52 (2), pages 495-503 such cured reaction products can be degraded by the acid catalyzed hydrolysis of the aminoacetal or thioacetal.

Whilst quantitative spectroscopic analysis of the degradation of fully cured resin under acidic conditions is difficult, the present inventors have herein assessed such degradation based on the size of cured resin before and after immersion in an aqueous acidic solution, constituted by water and acetic acid in a volume ratio of 1:1, at room temperature for 2 days (48 hours). The selected acid is not germane to the degradation and mineral acids such as HCl would also have a catalytic action: however the present protocol employed acetic acid.

Definitions

As used herein, the singular forms "a", "an" and "the" include plural referents unless the context clearly dictates otherwise.

The terms "comprising", "comprises" and "comprised of" as used herein are synonymous with "including", "includes", "containing" or "contains", and are inclusive or open-ended and do not exclude additional, non-recited members, elements or method steps. If used, the phrase "consisting of" is closed and excludes all additional elements. Further, the phrase "consisting essentially of" excludes additional material elements but allows the inclusion of non-material elements that do not substantially change the nature of the invention.

When amounts, concentrations, dimensions and other parameters are expressed in the form of a range, a preferable range, an upper limit value, a lower limit value or preferable upper and limit values, it should be understood that any ranges obtainable by combining any upper limit or preferable value with any lower limit or preferable value are also specifically disclosed, irrespective of whether the obtained ranges are clearly mentioned in the context.

The words "preferred", "preferably", "desirably" and "particularly" are used frequently herein to refer to embodiments of the disclosure that may afford particular benefits, under certain circumstances. However, the recitation of one or more preferable, preferred, desirable or particular embodiments does not imply that other embodiments are not useful and is not intended to exclude those other embodiments from the scope of the disclosure.

As used throughout this application, the word "may" is used in a permissive sense—that is meaning to have the potential to—rather than in the mandatory sense.

As used herein, "ambient conditions" refers to a set of parameters that include temperature, pressure and relative humidity of the immediate surroundings of the element in question. Herein ambient conditions are: a relative humidity of from 30 to 100% percent; a temperature in the range from 20 to 40° C.; and, a pressure of 0.9 to 1.1 bar.

As used herein "room temperature" is 23° C.±2° C.

As used herein, "degradable" refers to the capacity of a polymer or macromolecular compound to decompose to smaller environmentally innocuous molecules, for instance lower molecular weight species which are soluble or dispersible in water. Such degradation can be by various chemical mechanisms including, in particular, degradation by hydrolysis. The term degradation is intended to encompass biodegradation, wherein macromolecules are broken down to lower molecular weight species through the action of microorganisms and/or natural environmental factors. As such, the term "biodegradable polymer" refers to a polymer containing chemical linkages that can be broken down by inter alia hydrolysis, enzymes and/or microorganisms to form lower molecular weight species.

The term "reactive" as used herein, either alone or in the context of a "reactive composition" refers to substances that either can react upon contact or which can be caused to react through one or more of heat, irradiation, pressure, catalysis or contact with air or water.

As used herein, the terms "monomer" and "co-monomer" refer to a molecule that is capable of conversion to polymers, synthetic resins or elastomers by combination with itself or other similar molecules or compounds. The terms are not limited to small molecules but include oligomers, polymers and other large molecules capable of combining with themselves or other similar molecules or compounds.

As used herein, "macro-monomer" refers to a polymer having at least one functional group through which polymerization reactions can proceed. Macro-monomers are thus macromolecular monomers which can be converted to homo- or copolymers of defined structures. It is not precluded that a macro-monomer as used herein comprises more than one polymeric chain attached to one functional group.

As used herein, "polymerization conditions" are those conditions that cause the at least one monomer to form a polymer, such as temperature, pressure, atmosphere, ratio of starting components used in the polymerization mixture, reaction time, or external stimuli of the polymerization mixture. The polymerization process can be carried out in bulk, or solution, or other conventional polymerization modes. The process is operated at any of the reaction conditions appropriate to the polymerization mechanism.

As used herein, "step-growth polymerization" refers to a type of polymerization mechanism wherein bi- or multifunctional monomers react first to form dimers, then trimers, then eventually long chain polymers. In the event of multifunctional monomers, cross-linked polymers are produced.

As used herein, the term "ring-opening polymerization" denotes a polymerization in which a cyclic compound (monomer) is opened to form a linear polymer in the presence of an appropriate catalyst. The reaction system tends towards an equilibrium between the desired resulting high-molecular compounds, a mixture of cyclic compounds and/or linear oligomers, the attainment of which equilibrium largely depends on the nature and amount of the cyclic monomers, the catalyst used and on the reaction temperature. The use of solvents and/or emulsions in the polymerization is not recommended as their removal once the reaction is complete can be complex. That aside, an instructive disclosure of ring-opening polymerization may be found in inter alia Nuyken et al., *Ring-Opening Polymerization—An Introductory Review* Polymers 2013, 5, 361-403.

The term "orthoester" as used herein relates to compounds comprising a carbon atom linked to three alkoxy groups.

The name α-angelica lactone (CAS 591-12-8) is used synonymously with 5-methyl-3H-furan-2-one.

The term "exo" is being used in accordance with its standard definition in the art.

As used herein, the term "epoxide" denotes a compound characterized by the presence of at least one cyclic ether group, namely one wherein an ether oxygen atom is attached to two adjacent carbon atoms thereby forming a cyclic structure. The term is intended to encompass monoepoxide compounds, polyepoxide compounds (having two or more epoxide groups) and epoxide terminated prepolymers. The term "monoepoxide compound" is meant to denote epoxide compounds having one epoxy group. The term "polyepoxide compound" is meant to denote epoxide compounds having at least two epoxy groups. The term "diepoxide compound" is meant to denote epoxide compounds having two epoxy groups.

The epoxide may be unsubstituted but may also be inertly substituted. Exemplary inert substituents include chlorine, bromine, fluorine and phenyl.

As used herein, "$C_1$-$C_n$ alkyl" group refers to a monovalent group that contains 1 to n carbons atoms, that is a radical of an alkane and includes straight-chain and branched organic groups. As such, a "$C_1$-$C_{30}$ alkyl" group refers to a monovalent group that contains from 1 to 30 carbons atoms, that is a radical of an alkane and includes straight-chain and branched organic groups. Examples of alkyl groups include, but are not limited to: methyl; ethyl; propyl; isopropyl; n-butyl; isobutyl; sec-butyl; tert-butyl; n-pentyl; n-hexyl; n-heptyl; and, 2-ethylhexyl. In the present invention, such alkyl groups may be unsubstituted or may be substituted with one or more substituents such as halo, nitro, cyano, amido, amino, sulfonyl, sulfinyl, sulfanyl, sulfoxy, urea, thiourea, sulfamoyl, sulfamide and hydroxy. The halogenated derivatives of the exemplary hydrocarbon radicals listed above might, in particular, be mentioned as examples of suitable substituted alkyl groups. In general, however, a preference for unsubstituted alkyl groups containing from 1-18 carbon atoms ($C_1$-$C_{18}$ alkyl)—for example unsubstituted alkyl groups containing from 1 to 12 carbon atoms ($C_1$-$C_{12}$ alkyl)—should be noted.

The term "$C_3$-$C_{30}$ cycloalkyl" is understood to mean a saturated, mono-, bi- or tricyclic hydrocarbon group having from 3 to 30 carbon atoms. In general, a preference for cycloalkyl groups containing from 3-18 carbon atoms ($C_3$-$C_{18}$ cycloalkyl groups) should be noted. Examples of cycloalkyl groups include: cyclopropyl; cyclobutyl; cyclopentyl; cyclohexyl; cycloheptyl; cyclooctyl; adamantane; and, norbornane.

As used herein, an "$C_6$-$C_{18}$ aryl" group used alone or as part of a larger moiety—as in "aralkyl group"—refers to optionally substituted, monocyclic, bicyclic and tricyclic ring systems in which the monocyclic ring system is aromatic or at least one of the rings in a bicyclic or tricyclic ring system is aromatic. The bicyclic and tricyclic ring systems include benzofused 2-3 membered carbocyclic rings. Exemplary aryl groups include: phenyl; indenyl; naphthalenyl, tetrahydronaphthyl, tetrahydroindenyl; tetrahydroanthracenyl; and, anthracenyl. And a preference for phenyl groups may be noted.

As used herein, "$C_2$-$C_{12}$ alkenyl" refers to hydrocarbyl groups having from 2 to 12 carbon atoms and at least one unit of ethylenic unsaturation. The alkenyl group can be straight chained, branched or cyclic and may optionally be substituted. The term "alkenyl" also encompasses radicals having "cis" and "trans" configurations, or alternatively, "E" and "Z" configurations, as appreciated by those of ordinary skill in the art. In general, however, a preference for unsubstituted alkenyl groups containing from 2 to 10 ($C_{2-10}$) or 2 to 8 ($C_{2-8}$) carbon atoms should be noted. Examples of said $C_2$-$C_{12}$ alkenyl groups include, but are not limited to: —CH=CH$_2$; —CH=CHCH$_3$; —CH$_2$CH=CH$_2$; —C(=CH$_2$)(CH$_3$); —CH=CHCH$_2$CH$_3$; —CH$_2$CH=CHCH$_3$; —CH$_2$CH$_2$CH=CH$_2$; —CH=C(CH$_3$)$_2$; —CH$_2$C(=CH$_2$)(CH$_3$); —C(=CH$_2$)CH$_2$CH$_3$; —C(CH$_3$)=CHCH$_3$; —C(CH$_3$)CH=CH$_2$; —CH=CHCH$_2$CH$_2$CH$_3$; —CH$_2$CH=CHCH$_2$CH$_3$; —CH$_2$CH$_2$CH=CHCH$_3$; —CH$_2$CH$_2$CH$_2$CH=CH$_2$; —C(=CH$_2$)CH$_2$CH$_2$CH$_3$; —C(CH$_3$)=CHCH$_2$CH$_3$; —CH(CH$_3$)CH=CHCH; —CH(CH$_3$)CH$_2$CH=CH$_2$; —CH$_2$CH=C(CH$_3$)$_2$; 1-cyclopent-1-enyl; 1-cyclopent-2-enyl; 1-cyclopent-3-enyl; 1-cyclohex-1-enyl; 1-cyclohex-2-enyl; and, 1-cyclohexyl-3-enyl.

As used herein, "alkylaryl" refers to alkyl-substituted aryl groups and "substituted alkylaryl" refers to alkylaryl groups further bearing one or more substituents as set forth above.

The term "hetero" as used herein refers to groups or moieties containing one or more heteroatoms, such as N, O, Si and S. Thus, for example "heterocyclic" refers to cyclic groups having, for example, N, O, Si or S as part of the ring structure. "Heteroalkyl" and "heterocycloalkyl" moieties are alkyl and cycloalkyl groups as defined hereinabove, respectively, containing N, O, Si or S as part of their structure.

As used herein, the term "catalytic amount" means a sub-stoichiometric amount of catalyst relative to a reactant, except where expressly stated otherwise.

The term "photoinitiator" as used herein denotes a compound which can be activated by an energy-carrying activation beam—such as electromagnetic radiation—for instance upon irradiation therewith. The term is intended to encompass both photoacid generators and photobase generators. Specifically, the term "photoacid generator" refers to a compound or polymer which generates an acid for the catalysis of the acid hardening resin system upon exposure to actinic radiation. The term "photobase generator" means any material which when exposed to suitable radiation generates one or more bases.

The term "Lewis acid" used herein denotes any molecule or ion—often referred to as an electrophile—capable of combining with another molecule or ion by forming a covalent bond with two electrons from the second molecule or ion: a Lewis acid is thus an electron acceptor.

The molecular weights referred to in this specification can be measured with gel permeation chromatography (GPC) using polystyrene calibration standards, such as is done according to ASTM 3536.

As employed herein a "primary amino group" refers to an NH$_2$ group that is attached to an organic radical, and a "secondary amino group" refers to an NH group that is attached to two organic radicals, which may also together be part of a ring. Where used, the term "amine hydrogen" refers to the hydrogen atoms of primary and secondary amino groups.

The "amine equivalent weight" is a calculated value determined from the amine number. That amine number is determined by titration of the amine acetate ion by a dilute, typically 1N HCl solution. For a pure material, the amine number can be calculated using the molecular weights of the pure compound and KOH (56.1 g/mol). Instructive guidance may be found, for illustration, in https://dowac.custhelp.com/app/answers/detail/a_id/12987.

The term "Mannich Base" is used herein in accordance with its standard definition in the art as a ketonic amine obtainable from the condensation of a ketone with formaldehyde and ammonia or a primary or secondary amine (https://pubchem.ncbi.nlm.nih.gov/compound/9567537#section=Top).

The term "component" as used herein to define or characterize a composition refers to a component comprising at least one ingredient or compound, and which may also be a mixture of different ingredients or compounds.

"Two-component (2K) compositions" in the context of the present invention are understood to be compositions in which a binder component (A) and a hardener component (B) must be stored in separate vessels because of their (high) reactivity. The two components are mixed only shortly before application and then react, typically without additional activation, with bond formation and thereby formation of a polymeric network. However, catalysts may also be employed or higher temperatures applied in order to accelerate the cross-linking reaction.

Where mentioned, a calculated glass transition temperature ("T$_g$") of a polymer or co-polymer is that temperature which may be calculated by using the Fox equation (T. G. Fox, Bull. Am. Physics Soc., Volume 1, Issue No. 3, page 123(1956)). The glass transition temperatures of certain homo-polymers may be found in the published literature, such as in "*Polymer Handbook*", edited by J. Brandrup and E. H. Immergut, Interscience Publishers.

The actual glass transition temperature (T$_g$) of a polymer can be determined by differential scanning calorimetry (DSC). The use of DSC to determine T$_g$ is well known in the art, and is described by B. Cassel and M. P. DiVito in "*Use of DSC To Obtain Accurate Thermodynamic and Kinetic Data*", American Laboratory, January 1994, pp 14-19, and by B. Wunderlich in Thermal Analysis, Academic Press, Inc., 1990. The glass transition temperatures (T$_g$) specifically measured in the current patent application have been measured according to the methodology of Deutsches Institut für Normung (DIN) 11357.

The term "anhydrous" is intended to mean herein that the applicable reaction mixture or component comprises less than 0.25 wt. % of water, based on the weight of the mixture or component. The term "essentially free of solvent" should be interpreted analogously as meaning the relevant composition comprises less than 0.25 wt. % of solvent.

DETAILED DESCRIPTION OF THE INVENTION

Synthesis of the Functionalized α-Angelica Lactone (XOMAL)

The synthesis of the functionalized α-angelica lactone (XOMAL) is most broadly characterized by the following reaction scheme:

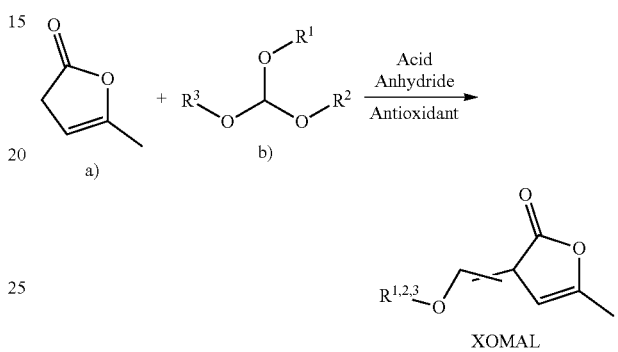

As noted above, the

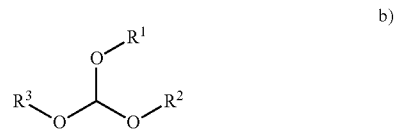

notation is used herein to indicate that all stereoisomers fall within the scope of this general formula (XOMAL).

There is no particular intention to limit the means by which the reactant alpha (α-) angelica lactone (a)) is obtained: aside from said compound being commercially available, it may also be synthesised via a multiplicity of synthesis routes known to the skilled artisan. Reference in this regard might be made to http://www.molbase.com/en/synthesis 591-12-8-moldata-4778.html. When expedient based on the synthesis route employed, the α-angelica lactone may be isolated and purified using methods known in the art. Mention in this regard may be made of extraction, evaporation, distillation and chromatography as suitable techniques.

The orthoester reactants having utility in the above described reaction scheme have the general formula (b)) herein below:

b)

$$R^3\underset{O}{\overset{O-R^1}{\underset{|}{C}}}O-R^2$$

in which: R$^1$, R$^2$ and R$^3$ are independently selected from C$_1$-C$_{30}$ alkyl, C$_3$-C$_{30}$ cycloalkyl, C$_6$-C$_{18}$ aryl and C$_2$-C$_{12}$ alkenyl groups.

In a preferred embodiment of the orthoesters of Formula (b)), R$^1$, R$^2$ and R$^3$ are independently selected from C$_1$-C$_{18}$ alkyl and C$_2$-C$_{12}$ alkenyl groups; R$^1$, R$^2$ and R$^3$ may for instance be independently selected from C$_1$-C$_{12}$ alkyl groups and $C_2$-$C_8$ alkenyl groups or independently selected from $C_1$-$C_6$ alkyl or $C_2$-$C_4$ alkenyl groups. Alternatively or additionally to the aforementioned embodiment, it is preferred that at least two of $R^1$, $R^2$ and $R^3$ in Formula (1) are the same.

Examples of suitable orthoesters (b)) for use in the present invention include but are not limited to: triethyl orthoformate ($R^1$=$R^2$=$R^3$=Et); trimethyl orthoformate ($R^1$=$R^2$=$R^3$=Me); tributyl orthoformate ($R^1$=$R^2$=$R^3$=Bu); tripropoxy orthoformate ($R^1$=$R^2$=$R^3$=nPr); diethyl vinyl orthoformate ($R^1$=$R^2$=Et, $R^3$=$CH_2$=$CH_2$); trioctadecyl orthoformate ($R^1$=$R^2$=$R^3$=$C_{18}H_{37}$); and, tripentyl orthoformate ($R^1$=$R^2$=$R^3$=$C_5H_{11}$).

As noted in the above scheme, the reaction is performed in the presence of an acid anhydride. Typically said acid anhydride is one of acetic anhydride, propionic anhydride, butyric anhydride or succinic anhydride. A preference for acetic anhydride is noted. That aside, the acid anhydride should be present in a catalytic amount which, in this regard, may include sub-stoichiometric amounts of said acid anhydride relative to the total number of moles of reactants (a), b)) but does not preclude the acid anhydride being present in molar excess—for instance up to a 20% molar excess—to the total number of moles of reactants (a), b)).

The reaction is also performed in the presence of a suitable antioxidant which will typically constitute up to 10 wt. % or up to 5 wt. %, based on the total weight of the reactants (a), b)) The use of one or more sterically hindered phenol—including but not limited to 2,6-di-tert-butyl-4-methylphenol (BHT) and/or butylated hydroxyanisole (BHA)—is preferred herein.

Whilst the presence of a co-catalyst is not required, it is also not precluded. The reaction between the orthoester and the α-angelica lactone may, in an embodiment, be performed in the presence of a catalytic amount of: a Lewis acid, such as $AlCl_3$, $TiCl_4$, $FeCl_3$, $SnCl_4$ or $ZnCl_2$; or, a strong protic acid selected from a group consisting of $H_2SO_4$, $HNO_3$, HCl, HBr, HI, trifluoroacetic acid (TFA), $H_3PO_4$, p-toluene sulfonic acid (p-TSA) and methanesulfonic acid (MSA).

The above reaction should be performed under anhydrous conditions. Exposure to atmospheric moisture may be avoided by providing the reaction vessel with an inert, dry gaseous blanket. Whilst dry nitrogen, helium and argon may be used as blanket gases, precaution should be used when common nitrogen gases are used as a blanket, because such nitrogen may not be dry enough on account of its susceptibility to moisture entrainment; the nitrogen may require an additional drying step before use herein.

The above described reaction may be carried out in the presence of a solvent. Inert solvents are preferred as solvents; these contain no reactive groups that react with the starting compounds. Inert, polar, aprotic solvents are particularly preferred. Named as such are, e.g., cyclic ether compounds, in particular tetrahydrofuran (THF).

The reaction temperature is typically at least 75° C. and preferably at least 100° C. Whilst the reaction temperature may be 200° C. or higher, it is preferred that the temperature does not exceed 175° C. or even 150° C. in order inter alia: to maintain workable reactor pressures; and, where applicable, to maintain adequate catalyst activity without deactivating or decomposing the catalyst. As the reaction is generally exothermic, some cooling might be required as it progresses.

The process pressure is not critical: as such, the reaction can be run at sub-atmospheric, atmospheric, or super-atmospheric pressures but pressures at or slightly above atmospheric pressure are preferred. Mention in this regard may be made of pressures of from 100 to 500 MPa or from 100 to 200 MPa.

The progress of the above reaction can be monitored by known techniques. For example, samples may be withdrawn from the reaction vessel and tested using Gas Chromatography (GC) with Flame Ionization Detection (FID).

The reaction product (XOMAL) may be isolated and purified using methods known in the art. Whilst mention in this regard may be made of extraction, filtration, evaporation, distillation and chromatography as suitable techniques it is most convenient that the product of the reaction be isolated by distilling off the solvent and any unreacted starting materials.

Curative Component

As noted above, the functionalized α-angelica lactone (XOMAL) is included in a reactive composition with: b) either one or both of: i) at least one polyamine having at least two amine hydrogens reactive toward epoxide groups; and, at least one mercapto compound having at least two mercapto groups reactive toward epoxide groups. By virtue of their reactivity with epoxy groups—by which reaction the epoxy resins become hardened—the component b) i) and/or b) ii) may be indicated hereinafter as a curative. The component parts b) i) and b) ii) necessarily include compounds possessing at least two epoxide reactive groups per molecule.

Component Part b) i)

The curative may comprise or consist of at least one polyamine having at least two amine hydrogens reactive toward epoxide groups. In particular, the desired polyamine may contain primary and/or secondary amine groups and have an equivalent weight per primary or secondary amine group of not more than 150, preferably not more than 125.

Suitable polyamines for use in the present invention, which may be used alone or in combination, include but are not limited to the following.

i) Aliphatic, cycloaliphatic or arylaliphatic primary diamines of which the following examples may be mentioned: 2,2-dimethyl-1,3-propanediamine; 1,3-pentanediamine (DAMP); 1,5-pentanediamine; 1,5-diamino-2-methylpentane (MPMD); 2-butyl-2-ethyl-1,5-pentanediamine (C11-neodiamine); 1,6-hexanediamine (hexamethylenediamine, HMDA); 2,5-dimethyl-1,6-hexanediamine; 2,2,4- and/or 2,4,4-trimethylhexamethylenediamine; 1,7-heptanediamine; 1,8-octanediamine; 1,9-nonanediamine; 1,10-decanediamine; 1,11-undecanediamine; 1,12-dodecanediamine; 1,2-, 1,3- and 1,4-diaminocyclohexane; bis(4-aminocyclohexyl) methane; bis(4-amino-3-methylcyclohexyl)methane; bis(4-amino-3-ethylcyclohexyl)methane; bis(4-amino-3,5-dimethylcyclohexyl)methane; bis(4-amino-3-ethyl-5-methylcyclohexyl)methane; 1-amino-3-aminomethyl-3,5,5-trimethylcyclohexane (isophorone diamine, IPDA); 2- and/or 4-methyl-1,3-diaminocyclohexane; 1,3-bis(aminomethyl)-cyclohexane; 1,4-bis(aminomethyl) cyclohexane; 2,5(2,6)-bis(aminomethyl)-bicyclo[2.2.1] heptane (norborane diamine, NBDA); 3(4),8(9)-bis(aminomethyl)tricyclo[5.2.1.0$^{2,6}$]-decane (TCD-diamine); 1,4-diamino-2,2,6-trimethylcyclohexane (TMCDA); 1,8-menthanediamine; 3,9-bis(3-aminopropyl)-2,4,8,10-tetraoxaspiro[5.5]undecane; and, 1,3-bis(aminomethyl)benzene (MXDA).

ii) Tertiary amine group-containing polyamines with two or three primary aliphatic amine groups of which the following specific examples may be mentioned: N,N'-bis(aminopropyl)-piperazine; N,N-bis(3-aminopropyl)methylamine; N,N-bis(3-aminopropyl)ethylamine; N,N-bis(3-aminopropyl)propylamine; N,N-bis(3-aminopropyl)cyclohexylamine; N,N-bis(3-aminopropyl)-2-ethyl-hexylamine; tris(2-aminoethyl)amine; tris(2-aminopropyl)amine; tris(3-aminopropyl)amine; and, the products from the double cyanoethylation and subsequent reduction of fatty amines derived from natural fatty acids, such as N,N-bis(3-aminopropyl)dodecylamine and N,N-bis(3-aminopropyl)tallow alkylamine, commercially available as Triameen® Y12D and Triameen® YT (from Akzo Nobel).

iii) Ether group-containing aliphatic primary polyamines of which the following specific examples may be mentioned: bis(2-aminoethyl)ether; 3,6-dioxaoctane-1,8-diamine; 4,7-dioxadecane-1,10-diamine; 4,7-dioxadecane-2,9-diamine; 4,9-dioxadodecane-1,12-diamine; 5,8-dioxadodecane-3,10-diamine; 4,7,10-trioxatridecane-1,13-diamine and higher oligomers of these diamines; bis(3-aminopropyl)polytetrahydrofuranes and other polytetrahydrofuran diamines; cycloaliphatic ether group-containing diamines obtained from the propoxylation and subsequent amination of 1,4-dimethylolcyclohexane, such as that material commercially available as Jeffamine® RFD-270 (from Huntsman); polyoxyalkylenedi- or -triamines obtainable as products from the amination of polyoxyalkylenedi- and -triols and which are commercially available under the name of Jeffamine® (from Huntsman), under the name of polyetheramine (from BASF) or under the name of PC Amines® (from Nitroil). A particular preference may be noted for the use of Jeffamine® D-230, Jeffamine® D-400, Jeffamine® D-600, Jeffamine® D-2000, Jeffamine® D-4000, Jeffamine® T-403, Jeffamine® T-3000, Jeffamine® T-5000, Jeffamine® EDR-104, Jeffamine® EDR-148 and Jeffamine® EDR-176, as well as corresponding amines from BASF or Nitroil.

iv) Primary diamines with secondary amine groups of which the following examples may be mentioned: 3-(2-aminoethyl)aminopropylamine, bis(hexamethylene)triamine (BHMT); diethylenetriamine (DETA); triethylenetetramine (TETA); tetraethylenepentamine (TEPA); pentaethylenehexamine (PEHA); higher homologs of linear polyethyleneamines, such as polyethylene polyamines with 5 to 7 ethyleneamine units (so-called "higher ethylenepolyamine," HEPA); products from the multiple cyanoethylation or cyanobutylation and subsequent hydrogenation of primary di- and polyamines with at least two primary amine groups, such as dipropylenetriamine (DPTA), N-(2-aminoethyl)-1,3-propanediamine (N3-amine), N,N'-bis(3-aminopropyl)ethylenediamine (N4-amine), N,N'-bis(3-aminopropyl)-1,4-diaminobutane, N5-(3-aminopropyl)-2-methyl-1,5-pentanediamine, N3-(3-aminopentyl)-1,3-pentanediamine, N5-(3-amino-1-ethylpropyl)-2-methyl-1,5-pentanediamine or N,N'-bis(3-amino-1-ethylpropyl)-2-methyl-1,5-pentanediamine.

v) Polyamines with one primary and at least one secondary amino group of which the following examples may be mentioned: N-butyl-1,2-ethanediamine; N-hexyl-1,2-ethanediamine; N-(2-ethylhexyl)-1,2-ethanediamine; N-cyclohexyl-1,2-ethanediamine; 4-aminomethyl-piperidine; N-(2-aminoethyl)piperazine; N-methyl-1,3-propanediamine; N-butyl-1,3-propanediamine; N-(2-ethylhexyl)-1,3-propanediamine; N-cyclohexyl-1,3-propanediamine; 3-methylamino-1-pentylamine; 3-ethylamino-1-pentylamine; 3-cyclohexylamino-1-pentylamine; fatty diamines such as N-cocoalkyl-1,3-propanediamine; products from the Michael-type addition reaction of primary aliphatic diamines with acrylonitrile, maleic or fumaric acid diesters, citraconic acid diesters, acrylic and methacrylic acid esters, acrylic and methacrylic acid amides and itaconic acid diesters, reacted in a 1:1 molar ratio; products from the partial reductive alkylation of primary polyamines with aldehydes or ketones, especially N-monoalkylation products of the previously mentioned polyamines with two primary amine groups and in particular of 1,6-hexanediamine, 1,5-diamino-2-methylpentane, 1,3-bis(aminomethyl)cyclohexane, 1,4-bis(aminomethyl)cyclohexane, 1,3-bis(aminomethyl)benzene, BHMT, DETA, TETA, TEPA, DPTA, N3-amine and N4-amine, wherein preferred alkyl groups are benzyl, isobutyl, hexyl and 2-ethylhexyl; and, partially styrenated polyamines such as those commercially available as Gaskamine® 240 (from Mitsubishi Gas Chemical).

vi) Secondary diamines and, in particular, N,N'-dialkylation products of the previously mentioned polyamines with two primary amine groups, especially N,N'-dialkylation products of 1,6-hexanediamine, 1,5-diamino-2-methylpentane, 1,3-bis(aminomethyl)cyclohexane, 1,4-bis(aminomethyl)-cyclohexane, 1,3-bis(aminomethyl)benzene, BHMT, DETA, TETA, TEPA, DPTA, N3-amine or N4-amine, wherein preferred alkyl groups are 2-phenylethyl, benzyl, isobutyl, hexyl and 2-ethylhexyl.

vii) Aromatic polyamines of which mention may be made of: m- and p-phenylenediamine; 4,4'-, 2,4' and 2,2'-diaminodiphenylmethane; 3,3'-dichloro-4,4'-diaminodiphenylmethane (MOCA); 2,4- and 2,6-tolylenediamine; mixtures of 3,5-dimethylthio-2,4- and -2,6-tolylenediamine (available as Ethacure® 300 from Albermarle); mixtures of 3,5-diethyl-2,4- and -2,6-tolylene diamine (DETDA); 3,3',5,5'-tetraethyl-4,4'-diaminodiphenylmethane (M-DEA); 3,3',5,5'-tetraethyl-2,2'-dichloro-4,4'-diaminodiphenylmethane (M-CDEA); 3,3'-diisopropyl-5,5'-dimethyl-4,4'-diaminodiphenylmethane (M-MIPA); 3,3',5,5'-tetraisopropyl-4,4'-diaminodiphenylmethane (M-DIPA); 4,4'-diamino diphenylsulfone (DDS); 4-amino-N-(4-aminophenyl)benzenesulfonamide; 5,5'-methylenedianthranilic acid; dimethyl-(5,5'-methylenedianthranilate); 1,3-propylene-bis (4-aminobenzoate); 1,4-butylene-bis(4-aminobenzoate); polytetramethylene oxide-bis(4-aminobenzoate) (available as Versalink® from Air Products); 1,2-bis(2-aminophenylthio)ethane, 2-methylpropyl-(4-chloro-3,5-diaminobenzoate); and, tert.butyl-(4-chloro-3,5-diaminobenzoate).

viii) Polyamidoamines of which indicative members include the reaction products of monohydric or polyhydric carboxylic acids or the esters or anhydrides thereof, —in particular dimer fatty acids—and an aliphatic, cycloaliphatic or aromatic polyamine, for instance polyalkyleneamines such as DETA or TETA. Commercially available polyamidoamines include: Versamid® 100, 125, 140 and 150 (from Cognis); Aradur® 223, 250 and 848 (from Huntsman); Euretek® 3607 and 530 (from Huntsman); and, Beckopox® EH 651, EH 654, EH 655, EH 661 and EH 663 (from Cytec).

ix) Mannich bases and in particular the commercially available phenalkamines Cardolite® NC-541, NC-557, NC-558, NC-566, Lite 2001 and Lite 2002 (available from Cardolite), Aradur® 3440, 3441, 3442 and 3460 (available from Huntsman) and Beckopox® EH 614, EH 621, EH 624, EH 628 and EH 629 (available from Cytec).

Preferred among the aforementioned polyamines having at least two primary aliphatic amine groups are: isophorone diamine (IPDA); hexamethylene diamine (NMDA); 1,3-bis (amino-methyl)cyclohexane; 1,4-bis(aminomethyl)cyclohexane; bis(4-amino-cyclohexyl)methane; bis(4-amino-3-methylcyclohexyl)methane; NBDA; and, ether group-containing polyamines with an average molecular weight of up to 5000 g/mol, in particular up to 2000 g/mol. Particularly preferred among said ether group-containing polyamines are Jeffamine® D-230 and D-600 (available from Huntsman).

Component Part b) ii)

The curative may comprise or consist of at least one mercapto group-containing compound. Suitable mercapto-group containing compounds, which may be used alone or in combination, include but are not limited to the following.

Liquid mercaptan-terminated polysulfide polymers of which commercial examples include: Thiokol® polymers (available from Morton Thiokol), in particular the types LP-3, LP-33, LP-980, LP-23, LP-55, LP-56, LP-12, LP-31, LP-32 and LP-2 thereof; and, Thioplast® polymers (from Akzo Nobel), in particular the types G10, G112, G131, G1, G12, G21, G22, G44 and G4.

Mercaptan-terminated polyoxyalkylene ethers, obtainable by reacting polyoxyalkylenedi- and -triols either with epichlorohydrin or with an alkylene oxide, followed by sodium hydrogen sulfide.

Mercaptan-terminated compounds in the form of polyoxyalkylene derivatives, known under the trade name of Capcure® (from Cognis), in particular the types WR-8, LOF and 3-800 thereof.

Polyesters of thiocarboxylic acids of which particular examples include: pentaerythritol tetramercapto-acetate (PETMP); trimethylolpropane trimercaptoacetate (TMPMP); glycol dimercaptoacetate; and, the esterification products of polyoxyalkylene diols and triols, ethoxylated trimethylolpropane and polyester diols with thiocarboxylic acids such as thioglycolic acid and 2- or 3-mercaptopropionic acid.

2,4,6-trimercapto-1,3,5-triazine, 2,2'-(ethylenedioxy)-di-ethanethiol (triethylene glycol dimercaptan) and/or ethanedithiol.

A preference for the use of polyesters of thiocarboxylic acids and, in particular, for the use of at least one of pentaerythritol tetramercapto-acetate (PETMP), trimethylolpropane trimercaptoacetate (TMPMP) and glycol dimercaptoacetate is acknowledged.

Epoxide Compound

Epoxy resins as used herein may include mono-functional epoxy resins, multi- or poly-functional epoxy resins, and combinations thereof. The epoxy resins may be pure compounds but equally may be mixtures epoxy functional compounds, including mixtures of compounds having different numbers of epoxy groups per molecule. An epoxy resin may be saturated or unsaturated, aliphatic, cycloaliphatic, aromatic or heterocyclic and may be substituted. Further, the epoxy resin may also be monomeric or polymeric.

Without intention to limit the polymerization processes of present invention, illustrative monoepoxide monomers include: alkylene oxides; epoxy-substituted cycloaliphatic hydrocarbons, such as cyclohexene oxide, vinylcyclohexene monoxide, (+)-cis-limonene oxide, (+)-cis,trans-limonene oxide, (−)-cis,trans-limonene oxide, cyclooctene oxide, cyclododecene oxide and α-pinene oxide; epoxy-substituted aromatic hydrocarbons; monoepoxy substituted alkyl ethers of monohydric alcohols or phenols, such as the glycidyl ethers of aliphatic, cycloaliphatic and aromatic alcohols; monoepoxy-substituted alkyl esters of monocarboxylic acids, such as glycidyl esters of aliphatic, cycloaliphatic and aromatic monocarboxylic acids; monoepoxy-substituted alkyl esters of polycarboxylic acids wherein the other carboxy group(s) are esterified with alkanols; alkyl and alkenyl esters of epoxy-substituted monocarboxylic acids; epoxyalkyl ethers of polyhydric alcohols wherein the other OH group(s) are esterified or etherified with carboxylic acids or alcohols; and, monoesters of polyhydric alcohols and epoxy monocarboxylic acids, wherein the other OH group(s) are esterified or etherified with carboxylic acids or alcohols.

By way of example, the following glycidyl ethers might be mentioned as being particularly suitable monoepoxide monomers for use herein: methyl glycidyl ether; ethyl glycidyl ether; propyl glycidyl ether; butyl glycidyl ether; pentyl glycidyl ether; hexyl glycidyl ether; cyclohexyl glycidyl ether; octyl glycidyl ether; 2-ethylhexyl glycidyl ether; allyl glycidyl ether; benzyl glycidyl ether; phenyl glycidyl ether; 4-tert-butylphenyl glycidyl ether; 1-naphthyl glycidyl ether; 2-naphthyl glycidyl ether; 2-chlorophenyl glycidyl ether; 4-chlorophenyl glycidyl ether; 4-bromophenyl glycidyl ether; 2,4,6-trichlorophenyl glycidyl ether; 2,4,6-tribromophenyl glycidyl ether; pentafluorophenyl glycidyl ether; o-cresyl glycidyl ether; m-cresyl glycidyl ether; and, p-cresyl glycidyl ether.

In an important embodiment, the monoepoxide monomer conforms to Formula (III) herein below:

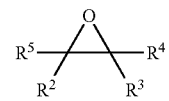

(III)

wherein: $R^2$, $R^3$, $R^4$ and $R^5$ may be the same or different and are independently selected from hydrogen, a halogen atom, a $C_1$-$C_8$ alkyl group, a $C_3$ to $C_{10}$ cycloalkyl group, a $C_2$-$C_{12}$ alkenyl, a $C_6$-$C_{18}$ aryl group or a $C_7$-$C_{18}$ aralkyl group, with the proviso that at least one of $R^3$ and $R^4$ is not hydrogen.

It is preferred that $R^2$, $R^3$ and $R^5$ are hydrogen and $R^4$ is either a phenyl group or a $C_1$-$C_8$ alkyl group and, more preferably, a $C_1$-$C_4$ alkyl group.

Having regard to this embodiment, exemplary monoepoxides include: ethylene oxide; 1,2-propylene oxide (propylene oxide); 1,2-butylene oxide; cis-2,3-epoxybutane; trans-2,3-epoxybutane; 1,2-epoxypentane; 1,2-epoxyhexane; 1,2-heptylene oxide; decene oxide; butadiene oxide; isoprene oxide; and, styrene oxide.

In the present invention, preference is given to using at least one monoepoxide monomer selected from the group consisting of: ethylene oxide; propylene oxide; cyclohexene oxide; (+)-cis-limonene oxide; (+)-cis,trans-limonene oxide; (−)-cis,trans-limonene oxide; cyclooctene oxide; and, cyclododecene oxide. It is particularly preferred if propylene oxide is used as a monomer: this statement of particular preference is intended to encompass said propylene oxide being either one of the epoxide monomers subjected to polymerization or the sole epoxide monomer.

Again, without intention to limit the polymerization processes of present invention, suitable polyepoxide monomers may be liquid, solid or in solution in solvent. Further, such polyepoxide compounds should have an epoxy equivalent weight of from 100 to 700 g/eq, for example from 120 to 320 g/eq. And generally, diepoxide compounds having epoxy equivalent weights of less than 500 or even less than 400 are preferred: this is predominantly from a costs standpoint, as in their production, lower molecular weight epoxy resins require more limited processing in purification.

As examples of types or groups of polyepoxide compounds which may be polymerized in present invention, mention may be made of: glycidyl ethers of polyhydric alcohols and polyhydric phenols; glycidyl esters of polycarboxylic acids; and, epoxidized polyethylenically unsaturated hydrocarbons, esters, ethers and amides.

Suitable diglycidyl ether compounds may be aromatic, aliphatic or cycloaliphatic in nature and, as such, can be derivable from dihydric phenols and dihydric alcohols. And useful classes of such diglycidyl ethers are: diglycidyl ethers of aliphatic and cycloaliphatic diols, such as 1,2-ethanediol, 1,4-butanediol, 1,6-hexanediol, 1,8-octanediol, 1,12-dodecanediol, cyclopentane diol and cyclohexane diol; bisphenol A based diglycidylethers; bisphenol F diglycidyl ethers; diglycidyl o-phthalate, diglycidyl isophthalate and diglycidyl terephthalate; polyalkyleneglycol based diglycidyl ethers, in particular polypropyleneglycol diglycidyl ethers; and, polycarbonatediol based glycidyl ethers. Other suitable diepoxides which might also be mentioned include: diepoxides of double unsaturated fatty acid C1-C18 alkyl esters; butadiene diepoxide; polybutadiene diglycidyl ether; vinylcyclohexene diepoxide; and, limonene diepoxide.

Further illustrative polyepoxide compounds include but are not limited to: glycerol polyglycidyl ether; trimethylolpropane polyglycidyl ether; pentaerythritol polyglycidyl ether; diglycerol polyglycidyl ether; polyglycerol polyglycidyl ether; and, sorbitol polyglycidyl ether.

And examples of highly preferred polyepoxide compounds include: bisphenol-A epoxy resins, such as DER™ 331, and DER™ 383; bisphenol-F epoxy resins, such as DER™ 354; bisphenol-NF epoxy resin blends, such as DER™ 353; aliphatic glycidyl ethers, such as DER™ 736; polypropylene glycol diglycidyl ethers, such as DER™ 732; solid bisphenol-A epoxy resins, such as DER™ 661 and DER™ 664 UE; solutions of bisphenol-A solid epoxy resins, such as DER™ 671-X75; epoxy novolac resins, such as DEN™ 438; brominated epoxy resins such as DER™ 542; castor oil triglycidyl ether, such as ERISYS™ GE-35H; polyglycerol-3-polyglycidyl ether, such as ERISYS™ GE-38; and, sorbitol glycidyl ether, such as ERISYS™ GE-60.

Whilst it is does not represent a preferred embodiment, the present invention does not preclude the curable compositions further comprising one or more cyclic monomers selected from the group consisting of: oxetanes; cyclic carbonates; cyclic anhydrides; and, lactones. The disclosures of the following citations may be instructive in disclosing suitable cyclic carbonate functional compounds: U.S. Pat. Nos. 3,535,342; 4,835,289; 4,892,954; UK Patent No. GB-A-1,485,925; and, EP-A-0 119 840. However, such cyclic co-monomers should constitute less than 20 wt. %, preferably less than 10 wt. % or less than 5 wt. %, based on the total weight of the epoxide compounds.

Reactive Compositions

As recited above and in the appended claims, the present invention provides a reactive composition comprising:
a) a functionalized α-angelica lactone (XOMAL) having the general formula

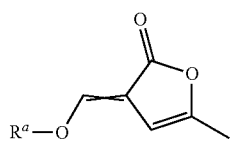

wherein $R^a$ is a $C_1$-$C_{30}$ alkyl, $C_3$-$C_{30}$ cycloalkyl, $C_6$-$C_{18}$ aryl or $C_2$-$C_{12}$ alkenyl group; and
b) either one or both of:
i) at least one polyamine having at least two amine hydrogens reactive toward epoxide groups; and,
ii) at least one mercapto compound having at least two mercapto groups reactive toward epoxide groups.

In an embodiment, the reactive composition is characterized in that the molar ratio of the alkoxy methylene (=C—$OR_a$) groups in part a) to the total of amine and mercapto groups in part b) is in the range from 0.5:1 to 2.5:1, for example from 0.8:1 to 2:1.

To form the reactive composition, parts a) and b) the reactive compounds should be mixed under sufficient shear forces to yield a homogeneous mixture. It is considered that this can be achieved without special conditions or special equipment. That said, suitable mixing devices might include: static mixing devices; magnetic stir bar apparatuses; wire whisk devices; augers; batch mixers; planetary mixers; C. W. Brabender or Banburry® style mixers; and, high shear mixers, such as blade-style blenders and rotary impellers.

The reactive composition may comprise a solvent in the presence of which the reaction of parts a) and b) would be carried out. Inert solvents are preferred as solvents; these contain no reactive groups that react with the starting compounds. Inert, polar, aprotic solvents are particularly preferred. Named as such are, e.g., cyclic ether compounds, in particular tetrahydrofuran (THF).

The reactive composition should not however comprise water: the reaction of parts a) and b) should ideally be performed under anhydrous conditions. Exposure to atmospheric moisture may be avoided by providing the storage vessel and any reaction vessel with an inert, dry gaseous blanket. Whilst dry nitrogen, helium and argon may be used as blanket gases, precaution should be used when common nitrogen gases are used as a blanket, because such nitrogen may not be dry enough on account of its susceptibility to moisture entrainment; the nitrogen may require an additional drying step before use herein.

Without being bound by theory, parts a) and b) can react by step-growth polymerization to yield a copolymer. Whilst there is no particular intention to limit the polymerization conditions, it is noted that such conditions may include thermal or photochemical induction. In the former case, the reactive composition may be exposed to temperatures in the range of from 20° C. to 120° C., preferably from 20° C. to 70° C., and in particular from 20° C. to 60° C. The temperature that is operative depends on the specific compounds present and the desired polymerization rate and can be determined in the individual case by the skilled artisan, using simple preliminary tests if necessary. Of course, temperatures of from 20° C. to 35° C. or from 20° C. to 30° C. are especially advantageous as they obviate the requirement to substantially heat the mixture from the usually prevailing ambient temperature. Where applicable, however, the temperature of the reactive compositions may be raised above the mixing temperature and/or the application temperature using conventional means, including microwave induction.

Where the polymerization process is thermally induced, it may be appropriate to include catalysts within the reactive composition in an amount up to 5 wt. %, for example up to 2 wt. %, based on the weight of the reactive compounds (a), b)). Without intention to the limit the catalysts used, mention may in particular be made of: i) tertiary amines, such as 1,4-diazabicyclo[2.2.2]octane, benzyldimethylamine, α-methylbenzyl dimethylamine, triethanolamine, dimethylamino propylamine, imidazoles—including N-methylimidazole, N-vinylimidazole and 1,2-dimethylimidazole—and salts of such tertiary amines; ii) quaternary ammonium salts, such as benzyltrimethyl ammonium chloride; iii) amidines, such as 1,8-diazabicyclo[5.4.0]undec-7-ene; iv) guanidines, such as 1,1,3,3-tetramethylguanidine; and, v) Mannich bases.

Where the reaction or step-growth polymerization is to be induced photo-chemically, the reactive composition may further comprise a photo-initiator which should be present in the composition in an amount of from 0.05 to 5.0 wt. %, for example from 0.05 to 2.0 wt. %, based on the weight of the reactive composition. The purpose of any subsequent irradiation of the reactive composition will be to generate the active species from the photoinitiator which initiates the reactions. Once that species is generated, the cure chemistry is subject to the same rules of thermodynamics as any chemical reaction: the reaction rate may be accelerated by heat.

In a particular embodiment, the photointiator comprises or consists of a photobase generator: upon exposure to UV radiation—typically in the wavelength from 320 to 420 nm—said photobase generator releases an amine, which catalyzes an addition of the reactive groups. The photobase generator is not specifically limited so long as it generates an amine directly or indirectly with light irradiation. However, suitable photobase generators which may be mentioned include: benzyl carbamates; benzoin carbamates; o-carbamoylhydroxyamines; O-carbamoyloximes; aromatic sulfonamides; alpha-lactams; N-(2-allylethenyl)amides; arylazide compounds, N-arylformamides, and 4-(ortho-nitrophenyl) dihydropyridines. As an exemplary photobase generator mention may be made of: 1,2-Diisopropyl-3-[Bis(dimethylamino)methylene guanidium 2-(3-benzoylphenyl) propionate, available from Fujifilm Wako Pure Chemical Corporation.

For completeness, the preparation of photobase generator compounds is known in the art and instructive references include: J. Cameron et al., Journal of the American Chemical Society, Vol. 113, No. 11, 4303-4313 (1991); J. Cameron et al., J. Polym. Mater. Sci. Eng., 64, 55 (1991); J. Cameron et al., J. Org. Chem., 55, 5919-5922 (1990); Sun et al., Journal of the American Chemical Society (2008), 130 (26), 8130-8131; Suyama et al., Progress in Polymer Science (2009), 34 (2), 194-209; Arimitsu et al., Journal of Photopolymer Science and Technology (2010), 23, 135-136; Kobayashi et al., Journal of Photopolymer Science and Technology (2018), 31, 107-112; and, U.S. Pat. No. 5,650,261 (Winkel). Moreover, photobase generators are further described in: M. Shirai et al. *Photochemical Reactions of Quatenary Ammonium Dithiocarbamates as Photobase Generators and Their Use in The Photoinitiated Thermal Crosslinking of Poly (gycidylmethacrylate)*, Journal of Polymer Science, Part A: Polymer Chemistry, Vol. 39, pp. 1329-1341 (2001); and, M. Shirai et al., *Photoacid and photobase generators: chemistry and applications to polymeric materials*, Progress in Polymer Science, Vol. 21, pp. 1-45, XP-002299394, 1996.

The polymerization process pressure is not critical: as such, the reaction of parts a) and b) can be run at sub-atmospheric, atmospheric, or super-atmospheric pressures but pressures at or slightly above atmospheric pressure are preferred. Mention in this regard may be made of pressures of from 100 to 500 MPa or from 100 to 200 MPa.

The progress of the reaction of parts a) and b) can be monitored by known techniques. For example, samples may be withdrawn from the reaction vessel and tested using Gas Chromatography (GC) with Flame Ionization Detection (FID).

The copolymer product may be isolated and purified using methods known in the art. Whilst mention in this regard may be made of extraction, filtration, evaporation, distillation and chromatography as suitable techniques it is most convenient that the copolymer product of the reaction be isolated by distilling off any solvent employed and any unreacted starting materials.

The copolymer obtained from the reactive composition as defined herein above and in the appended claims is within the scope of the present invention. As will be recognized by the skilled artisan, when the total of amine and mercapto-groups in part b) of that reactive composition is in molar excess of the alkoxy methylene (=C—OR$_a$) groups in part a), the copolymer obtained from the reaction will be amine or mercapto-functionalized: the copolymer will thus be reactive with epoxide compounds. The present invention thereby enables the synthesis, from the defined reactive composition, of a degradable, copolymer having at least two epoxide reactive groups and further enables the use of said copolymer as a hardener or curative for epoxide compounds.

Curable Compositions Based on Epoxy Resins

As noted above, the present invention provides a curable composition comprising:
a) a functionalized α-angelica lactone (XOMAL) having the general formula

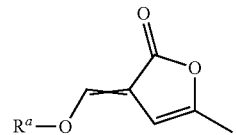

wherein R$^a$ is a C$_1$-C$_{30}$ alkyl, C$_3$-C$_{30}$ cycloalkyl, C$_6$-C$_{18}$ aryl or C$_2$-C$_{12}$ alkenyl group;
b) either one or both of:
  i) at least one polyamine having at least two amine hydrogens reactive toward epoxide groups; and,
  ii) at least one mercapto compound having at least two mercapto groups reactive toward epoxide groups; and,
c) at least one epoxide compound.

When formulating the curable composition, it is preferred that the composition in to to be characterized by a molar ratio of epoxy-reactive groups to epoxy groups from 0.95:1 to 1.5:1, for example from 0.95:1 to 1.1:1. Notably, the molar ratio of epoxy-reactive groups to epoxy groups of 1:1 is included within these stated ranges and itself represents a highly preferred molar ratio.

In an independent expression of the formulation of the composition which is not intended to be mutually exclusive of the above definition by molar ratio, the curable composition may comprise, based on the weight of the composition:
from 1 to 70 wt. % a) a functionalized α-angelica lactone (XOMAL) having the general formula:

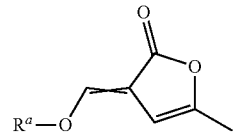

wherein R$^a$ is a C$_1$-C$_{30}$ alkyl, C$_3$-C$_{30}$ cycloalkyl, C$_6$-C$_{18}$ aryl or C$_2$-C$_{12}$ alkenyl group.
from 30 to 70 wt. % of b) a curative component, said component comprising:

i) at least one polyamine having at least two amine hydrogens reactive toward epoxide groups; and/or ii) at least one mercapto compound having at least two mercapto groups reactive toward epoxide groups; and, from 10 to 80 wt. % of c) at least one epoxide compound.

In an exemplary but non-limiting embodiment of the curable composition of the present invention, there is provided a curable composition comprising, based on the weight of the composition:

from 10 to 40 wt. % a) a functionalized α-angelica lactone (XOMAL) having the general formula:

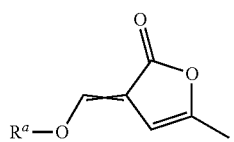

wherein $R^a$ is a $C_1$-$C_4$alkyl or $C_2$-$C_4$ alkenyl group;

from 20 to 50 wt. % of b) a curative component, said component comprising:

i) at least one polyamine having at least two amine hydrogens reactive toward epoxide groups, wherein said at least one polyamine contains primary and/or secondary amine groups and has an equivalent weight per primary or secondary amine group of not more than 150; and/or ii) polyester of a thiocarboxylic acid selected from the group consisting of pentaerythritol tetramercaptoacetate (PETMP), trimethylolpropane trimercaptoacetate (TMPMP), glycol dimercaptoacetate and mixtures thereof; and, from 10 to 50 wt. % of c) at least one polyepoxide compound selected from the group consisting of: glycidyl ethers of polyhydric alcohols; gycidyl ethers of polyhydric phenols; and, glycidyl esters of polycarboxylic acids.

The above defined curable compositions—which may find utility as coating, sealant or adhesive compositions, as a thermosetting composition for composite materials—will typically further comprise adjuvants and additives that can impart improved properties to these compositions. For instance, the adjuvants and additives may impart one or more of: improved elastic properties; improved elastic recovery; longer enabled processing time; faster curing time; and, lower residual tack. Included among such adjuvants and additives—which independently of one another may be included in single components or both components of a two (2K) component composition—are catalysts, plasticizers, stabilizers including UV stabilizers, antioxidants, tougheners, fillers, reactive diluents, drying agents, adhesion promoters, fungicides, flame retardants, rheological adjuvants, color pigments or color pastes, and/or optionally also, to a small extent, non-reactive diluents.

For completeness, it is noted that in general adjunct materials and additives which contain epoxide-reactive groups will be blended into the hardener or curative component of a two (2K) component composition. Materials that contain epoxide groups or which are reactive with the hardener(s) are generally formulated into the epoxide-containing component of a two (2K) component composition. Unreactive materials may be formulated into either or both of the two components.

Suitable catalysts are substances that promote the reaction between the epoxide groups and the epoxide-reactive groups, for instance the reaction between the amine groups and the epoxide groups. A specific example relates to the use of an amine catalyst which functions by de-protonation of reactive thiol (—SH) groups present to thiolate (—S⁻), which thiolate reacts with epoxy group by nucleophilic ring opening polymerization.

Without intention to the limit the catalysts used in the present invention, mention may be made of the following suitable catalysts: i) acids or compounds hydrolyzable to acids, in particular a) organic carboxylic acids, such as acetic acid, benzoic acid, salicylic acid, 2-nitrobenzoic acid and lactic acid; b) organic sulfonic acids, such as methanesulfonic acid, p-toluenesulfonic acid and 4-dodecylbenzenesulfonic acid; c) sulfonic acid esters; d) inorganic acids, such as phosphoric acid; e) Lewis acid compounds, such as $BF_3$ amine complexes, $SbF_6$ sulfonium compounds, bis-arene iron complexes; f) Bronsted acid compounds, such as pentafluoroantimonic acid complexes; and, e) mixtures of the aforementioned acids and acid esters; ii) tertiary amines, such as 1,4-diazabicyclo[2.2.2]octane, benzyldimethylamine, α-methylbenzyl dimethylamine, triethanolamine, dimethylamino propylamine, imidazoles—including N-methyl-imidazole, N-vinylimidazole and 1,2-dimethylimidazole—and salts of such tertiary amines; iii) quaternary ammonium salts, such as benzyltrimethyl ammonium chloride; iv) amidines, such as 1,8-diazabicyclo[5.4.0]undec-7-ene; v) guanidines, such as 1,1,3,3-tetramethylguanidine; vi) phenols, in particular bisphenols; vii) phenol resins; viii) Mannich bases; and, ix) phosphites, such as di- and triphenylphosphites.

In an embodiment, an amine catalyst for the curing a composition based on the epoxy resin may be photobase generator: upon exposure to UV radiation—typically in the wavelength from 320 to 420 nm—said photobase generator releases an amine, which catalyzes the addition of the epoxide reactive groups to the epoxide. The photobase generator is not specifically limited so long as it generates an amine directly or indirectly with light irradiation. However, suitable photobase generators which may be mentioned include: benzyl carbamates; benzoin carbamates; o-carbamoylhydroxyamines; O-carbamoyloximes; aromatic sulfonamides; alpha-lactams; N-(2-allylethenyl)amides; arylazide compounds, N-arylformamides, and 4-(ortho-nitrophenyl) dihydropyridines. As an exemplary photobase generator mention may be made of: 1,2-Diisopropyl-3-[Bis(dimethylamino)methylene guanidium 2-(3-benzoylphenyl) propionate, available from Fujifilm Wako Pure Chemical Corporation.

For completeness, the preparation of photobase generator compounds is known in the art and instructive references include: J. Cameron et al., Journal of the American Chemical Society, Vol. 113, No. 11, 4303-4313 (1991); J. Cameron et al., J. Polym. Mater. Sci. Eng., 64, 55 (1991); J. Cameron et al., J. Org. Chem., 55, 5919-5922 (1990); Sun et al., Journal of the American Chemical Society (2008), 130 (26), 8130-8131; Suyama et al., Progress in Polymer Science (2009), 34 (2), 194-209; Arimitsu et al., Journal of Photopolymer Science and Technology (2010), 23, 135-136; Kobayashi et al., Journal of Photopolymer Science and Technology (2018), 31, 107-112; and, U.S. Pat. No. 5,650,261 (Winkel). Moreover, photobase generators are further described in: M. Shirai et al. *Photochemical Reactions of Quaternary Ammonium Dithiocarbamates as Photobase Generators and Their Use in The Photoinitiated Thermal Crosslinking of Poly (gycidylmethacrylate)*, Journal of Polymer Science, Part A:

Polymer Chemistry, Vol. 39, pp. 1329-1341 (2001); and, M. Shirai et al., *Photoacid and photobase generators: chemistry and applications to polymeric materials*, Progress in Polymer Science, Vol. 21, pp. 1-45, XP-002299394, 1996.

In an alternative embodiment, an acid catalyst may be selected from photoacid generators (PAGs): upon irradiation with light energy, ionic photoacid generators undergo a fragmentation reaction and release one or more molecules of Lewis or Bronsted acid that catalyze the ring opening and addition of the pendent epoxide groups to form a crosslink. Useful photoacid generators are thermally stable, do not undergo thermally induced reactions with the forming copolymer and are readily dissolved or dispersed in the curable compositions. Photoacid generators are known in the art and instructive reference may be made to: K. Dietliker, *Chemistry and Technology of UV and EB Formulation for Coatings, Inks and Paints*, Vol. III, SITA Technology Ltd., London (1991); and, Kirk-Othmer *Encyclopedia of Chemical Technology*, 4.Sup.Th Edition, Supplement Volume, John Wiley and Sons, New York, pp 253-255.

Exemplary cations which may be used as the cationic portion of the ionic PAG of the invention include organic onium cations such as those described in U.S. Pat. Nos. 4,250,311, 3,113,708, 4,069,055, 4,216,288, 5,084,586, 5,124,417, and, U.S. Pat. No. 5,554,664. The references specifically encompass aliphatic or aromatic Group IVA and VIIA (CAS version) centered onium salts, with a preference being noted for I-, S-, P-, Se- N- and C-centered onium salts, such as those selected from sulfoxonium, iodonium, sulfonium, selenonium, pyridinium, carbonium and phosphonium.

As is known in the art, the nature of the counter-anion in the ionic photoacid generator (PAG) can influence the rate and extent of cationic addition polymerization of the epoxy groups. For illustration, Crivello et al. Chem. Mater., 4, 692, (1992) reports that the order of reactivity among commonly used nucleophilic anions is $SbF_6^->AsF_6^->PF_6^->BF_4^-$. The influence of the anion on reactivity has been ascribed to three principle factors which the skilled artisan should compensate for in the present invention: (1) the acidity of the protonic or Lewis acid generated; (2) the degree of ion-pair separation in the propagating cationic chain; and, (3) the susceptibility of the anions to fluoride abstraction and consequent chain termination.

It is not precluded that the compositions of the present invention include alternative photoinitiator compounds to the photobase generator and photoacid generator compounds mentioned herein above, which photoinitiator compound(s) would initiate the polymerization or hardening of the compositions upon irradiation with actinic radiation. It is noted that photo-polymerizable compositions of the present invention can be cationically polymerizable or free-radically polymerizable: whilst epoxy groups are cationically active, the election of a free-radical polymerization mechanism imposes the requirement that the composition must contain a compound possessing a free-radically active, unsaturated group such as an acrylate compound, a (meth)acrylate compound, an epoxy-functional acrylate, an epoxy functional (meth)acrylate or a combination thereof. Applying that election, the preferred photoinitiators would be photoactive compounds that undergo a Norrish I cleavage to generate free radicals that can initiate by addition to the acrylic double bonds.

In to to photoinitiators should be present in the photo-polymerizable composition in amount of from 0.1 to 1.0 parts by weight based on 100 parts of the reactant monomers.

The use of a photobase generator, photoacid generator and radical photoinitiators may produce residue compounds from the photochemical reaction. The residues may be detected by conventional analytical techniques such as: infrared, ultraviolet and NMR spectroscopy; gas or liquid chromatography; and, mass spectroscopy. Thus, the present invention may comprise cured (epoxy) matrix copolymers and detectable amounts of residues from a photobase/acid generator. Such residues are present in small amounts and do not normally interfere with the desired physiochemical properties of the product.

Without intention to limit the present invention, the monomer mixture and the photoinitiator may be irradiated with activating UV radiation to polymerize the monomer component(s). UV light sources can be of two types: i) relatively low light intensity sources such as backlights which provide generally 10 $mW/cm^2$ or less over a wavelength range of from 280 to 400 nanometers; or, ii) relatively high light intensity sources, such as medium pressure mercury lamps, which provide intensities generally greater than 10 $mW/cm^2$, for example between 15 and 750 $mW/cm^2$ or more usually between 15 and 450 $mW/cm^2$.

The purpose of the irradiation is to generate the active species from the photoinitiator which initiates the cure reactions. Once that species is generated, the cure chemistry is subject to the same rules of thermodynamics as any chemical reaction: the reaction rate may be accelerated by heat. The practice of using thermal treatments to enhance the cationic UV cure of monomers is generally known in the art, with an illustrative instructive reference being Crivello et al., "*Dual Photo-and thermally initiated cationic polymerization of epoxy monomers*," Journal of Polymer Science A, Polymer Chemistry., Vol. 44, Issue: 23, pp. 6750-6764, (Dec. 1, 2006).

As would be recognized by the skilled artisan, photosensitizers can be incorporated into the compositions to improve the efficiency with which the photoinitiators use the energy delivered. Photosensitizers are typically used in an amount of from 5 to 25 wt. %, based on the weight of the photoinitiator.

A "plasticizer" for the purposes of this invention is a substance that decreases the viscosity of the composition and thus facilitates its processability. Herein the plasticizer may constitute up to 40 wt. % or up to 20 wt. %, based on the total weight of the composition, and is preferably selected from the group consisting of: polydimethylsiloxanes (PDMS); diurethanes; ethers of monofunctional, linear or branched C4-C16 alcohols, such as Cetiol OE (obtainable from Cognis Deutschland GmbH, Düsseldorf); esters of abietic acid, butyric acid, thiobutyric acid, acetic acid, propionic acid esters and citric acid; esters based on nitrocellulose and polyvinyl acetate; fatty acid esters; dicarboxylic acid esters; esters of OH-group-carrying or epoxidized fatty acids; glycolic acid esters; benzoic acid esters; phosphoric acid esters; sulfonic acid esters; trimellitic acid esters; epoxidized plasticizers; polyether plasticizers, such as end-capped polyethylene or polypropylene glycols; polystyrene; hydrocarbon plasticizers; chlorinated paraffin; and, mixtures thereof. It is noted that, in principle, phthalic acid esters can be used as the plasticizer but these are not preferred due to their toxicological potential. It is preferred that the plasticizer comprises or consists of one or more polydimethylsiloxane (PDMS).

"Stabilizers" for purposes of this invention are to be understood as antioxidants, UV stabilizers or hydrolysis stabilizers. Herein stabilizers may constitute in to to up to 10 wt. % or up to 5 wt. %, based on the total weight of the composition. Standard commercial examples of stabilizers suitable for use herein include: sterically hindered phenols; thioethers; benzotriazoles; benzophenones; benzoates; cyanoacrylates; acrylates; amines of the hindered amine light stabilizer (HALS) type; phosphorus; sulfur; and, mixtures thereof.

Those compositions of the present invention may optionally contain a toughening rubber which is desirably present in the form of a rubber-modified epoxy resin, in the form of core-shell particles or a combination thereof. The toughening rubber should have a glass transition temperature ($T_g$) of no greater than −25° C.: preferably at least a portion of the toughening rubber should have a glass transition temperature ($T_g$) of −40° C. or lower, more preferably −50° C. or lower and even more preferably −70° C. or lower.

As noted, the compositions according to the present invention can additionally contain fillers. Suitable here are, for example, chalk, lime powder, precipitated and/or pyrogenic silicic acid, zeolites, bentonites, magnesium carbonate, diatomite, alumina, clay, talc, titanium oxide, iron oxide, zinc oxide, sand, quartz, flint, mica, glass powder, and other ground mineral substances. Organic fillers can also be used, in particular carbon black, graphite, wood flour, wood fibers, sawdust, cellulose, cotton, pulp, cotton, wood chips, chopped straw, chaff, ground walnut shells, and other chopped fibers. Short fibers such as glass fibers, glass filament, polyacrylonitrile, carbon fibers, Kevlar fibers, or polyethylene fibers can also be added. Aluminum powder is likewise suitable as a filler.

The pyrogenic and/or precipitated silicic acids advantageously have a BET surface area from 10 to 90 $m^2/g$. When they are used, they do not cause any additional increase in the viscosity of the composition according to the present invention, but do contribute to strengthening the cured composition.

It is likewise conceivable to use pyrogenic and/or precipitated silicic acids having a higher BET surface area, advantageously from 100 to 250 $m^2/g$, in particular from 110 to 170 $m^2/g$, as a filler: because of the greater BET surface area, the effect of strengthening the cured composition is achieved with a smaller proportion by weight of silicic acid.

Also suitable as fillers are hollow spheres having a mineral shell or a plastic shell. These can be, for example, hollow glass spheres that are obtainable commercially under the trade names Glass Bubbles®. Plastic-based hollow spheres, such as Expancel® or Dualite®, may be used and are described in EP 0 520 426 B1: they are made up of inorganic or organic substances and each have a diameter of 1 mm or less, preferably 500 µm or less.

Fillers which impart thixotropy to the composition may be preferred for many applications: such fillers are also described as rheological adjuvants, e.g. hydrogenated castor oil, fatty acid amides, or swellable plastics such as PVC.

The total amount of fillers present in the compositions of the present invention will preferably be from 1 to 80 wt. %, and more preferably from 5 to 60 wt. %, based on the total weight of the composition. The desired viscosity of the curable composition will typically be determinative of the total amount of filler added and it is submitted that in order to be readily extrudable out of a suitable dispensing apparatus—such as a tube—the curable compositions should possess a viscosity of from 3000 to 150,000, preferably from 40,000 to 80,000 mPas, or even from 50,000 to 60,000 mPas.

Examples of suitable pigments are titanium dioxide, iron oxides, or carbon black.

In order to enhance shelf life even further, it is often advisable to further stabilize the compositions of the present invention with respect to moisture penetration through using drying agents. A need also occasionally exists to lower the viscosity of an adhesive or sealant composition according to the present invention for specific applications, by using reactive diluent(s). The total amount of reactive diluents present will typically be up to 15 wt. %, and preferably from 1 and 5 wt. %, based on the total weight of the composition.

The presence of non-reactive diluents in the compositions of the present invention is also not precluded where this can usefully moderate the viscosities thereof. For instance, but for illustration only, the compositions may contain one or more of: xylene; 2-methoxyethanol; dimethoxyethanol; 2-ethoxyethanol; 2-propoxyethanol; 2-isopropoxyethanol; 2-butoxyethanol; 2-phenoxyethanol; 2-benzyloxyethanol; benzyl alcohol; ethylene glycol; ethylene glycol dimethyl ether; ethylene glycol diethyl ether; ethylene glycol dibutyl ether; ethylene glycol diphenyl ether; diethylene glycol; diethylene glycol-monomethyl ether; diethylene glycol-monoethyl ether; diethylene glycol-mono-n-butyl ether; diethylene glycol dimethyl ether; diethylene glycol diethyl ether; diethylene glycoldi-n-butylyl ether; propylene glycol butyl ether; propylene glycol phenyl ether; dipropylene glycol; dipropylene glycol monomethyl ether; dipropylene glycol dimethyl ether; dipropylene glycoldi-n-butyl ether; N-methylpyrrolidone; diphenylmethane; diisopropylnaphthalene; petroleum fractions such as Solvesso® products (available from Exxon); alkylphenols, such as tert-butylphenol, nonylphenol, dodecylphenol and 8,11,14-pentadecatrienylphenol; styrenated phenol; bisphenols; aromatic hydrocarbon resins especially those containing phenol groups, such as ethoxylated or propoxylated phenols; adipates; sebacates; phthalates; benzoates; organic phosphoric or sulfonic acid esters; and sulfonamides.

The above aside, it is preferred that said non-reactive diluents constitute less than 10 wt. %, in particular less than than 5 wt. % or less than 2 wt. %, based on the total weight of the composition.

For completeness, the compositions of the present invention may comprise one or more monoamines, such as hexylamine and benzylamine.

Methods and Applications

To form the defined curable composition—such as a coating, sealant or adhesive composition—the reactive compounds are brought together and mixed. As is known in the art, to form one component (1K) curable compositions, the elements of the composition are brought together and homogeneously mixed under conditions which inhibit or prevent the reactive components from reacting: as would be readily comprehended by the skilled artisan, this might include mixing conditions which limit or prevent exposure to moisture or irradiation or which limit or prevent the activation of a constituent latent catalyst. As such, it will often be preferred that the curative elements are not mixed by hand but are instead mixed by machine—a static or dynamic mixer, for example—in pre-determined amounts under anhydrous conditions without intentional photo-irradiation.

For the two component (2K) curable compositions, the reactive components are brought together and mixed in such a manner as to induce the hardening thereof. For both one (1K) and two (2K) component compositions, the reactive compounds should be mixed under sufficient shear forces to yield a homogeneous mixture. It is considered that this can be achieved without special conditions or special equipment. That said, suitable mixing devices might include: static mixing devices; magnetic stir bar apparatuses; wire whisk devices; augers; batch mixers; planetary mixers; C. W. Brabender or Banbury® style mixers; and, high shear mixers, such as blade-style blenders and rotary impellers.

For small-scale liner applications in which volumes of less than 2 liters will generally be used, the preferred packaging for the two component (2K) compositions will be side-by-side double cartridges or coaxial cartridges, in which two tubular chambers are arranged alongside one another or inside one another and are sealed with pistons: the driving of these pistons allows the components to be extruded from the cartridge, advantageously through a closely mounted static or dynamic mixer. For larger volume applications, the two components of the composition may advantageously be stored in drums or pails: in this case the two components are extruded via hydraulic presses, in particular by way of follower plates, and are supplied via pipelines to a mixing apparatus which can ensure fine and highly homogeneous mixing of the hardener and binder components. In any event, for any package it is important that the binder component be disposed with an airtight and moisture-tight seal, so that both components can be stored for a long time, ideally for 12 months or longer.

Non-limiting examples of two component dispensing apparatuses and methods that may be suitable for the present invention include those described in U.S. Pat. Nos. 6,129, 244 and 8,313,006.

Where applicable, two (2K) component curable compositions should broadly be formulated to exhibit an initial viscosity—determined immediately after mixing, for example, up to two minutes after mixing—of less than 200000 mPas, for instance less than 100000 mPa·s, at 25° C. Independently of or additional to said viscosity characteristics, the two (2K) component composition should be formulated to be bubble (foam) free upon mixing and subsequent curing. Moreover, the two component (2K) composition should further be formulated to demonstrate at least one, desirably at least two and most desirably all of the following properties: i) a long pot life, typically of at least 30 minutes and commonly of at least 60 or 120 minutes, which pot life should be understood herein to be the time after which the viscosity of a mixture at 20° C. will have risen to more than 50,000 mPas; ii) a maximum exotherm temperature of no greater than 120° C., preferably no greater than 100° C. and more preferably no greater than 80° C.; and, iii) a Shore A hardness of at least 50, preferably at 60 and more preferably at least 70 after being cured and stored for 7 days at room temperature and 50% relative humidity.

The curing of the compositions of the invention typically occurs at temperatures in the range of from −10° C. to 120° C., preferably from 0° C. to 70° C., and in particular from 20° C. to 60° C. The temperature that is suitable depends on the specific compounds present and the desired curing rate and can be determined in the individual case by the skilled artisan, using simple preliminary tests if necessary. Of course, curing at temperatures of from 10° C. to 35° C. or from 20° C. to 30° C. is especially advantageous as it obviates the requirement to substantially heat or cool the mixture from the usually prevailing ambient temperature. Where applicable, however, the temperature of the mixture formed from the respective components of a two (2K) component composition may be raised above the mixing temperature and/or the application temperature using conventional means including microwave induction.

The curable compositions according to the invention may find utility inter alia in: varnishes; inks; elastomers; foams; binding agents for fibers and/or particles; the coating of glass; the coating of mineral building materials, such as lime- and/or cement-bonded plasters, gypsum-containing surfaces, fiber cement building materials and concrete; the coating and sealing of wood and wooden materials, such as chipboard, fiber board and paper; the coating of metallic surfaces; the coating of asphalt- and bitumen-containing pavements; the coating and sealing of various plastic surfaces; and, the coating of leather and textiles.

It is also considered that the compositions of the present invention are suitable as pourable sealing compounds for electrical building components such as cables, fiber optics, cover strips or plugs. The sealants may serve to protect those components against the ingress of water and other contaminants, against heat exposure, temperature fluctuation and thermal shock, and against mechanical damage.

By virtue of the fact that the compositions of the present invention are capable of creating a high binding strength in a short time, often at room temperature, the compositions are optimally used for forming composite structures by surface-to-surface bonding of the same or different materials to one another. The binding together of wood and wooden materials and the binding together of metallic materials may be mentioned as exemplary adhesive applications of the present compositions.

In each of the above described applications, the compositions may applied by conventional application methods such as: brushing; roll coating using, for example, a 4-application roll equipment where the composition is solvent-free or a 2-application roll equipment for solvent-containing compositions; doctor-blade application; printing methods; and, spraying methods, including but not limited to air-atomized spray, air-assisted spray, airless spray and high-volume low-pressure spray. For coating and adhesive applications, it is recommended that the compositions be applied to a wet film thickness of from 10 to 500 µm. The application of thinner layers within this range is more economical and provides for a reduced likelihood of thick cured regions that may—for coating applications—require sanding. However, great control must be exercised in applying thinner coatings or layers so as to avoid the formation of discontinuous cured films.

For completeness, it is noted that the present invention does not preclude the preparation of epoxy adhesives in the form of "film adhesive". A pre-polymer mixture of epoxy, XOMAL, hardener, and other desired components is applied as a coating onto a polymer film substrate, rolled up and stored at a sufficiently low temperature to inhibit the chemical reactions between the components. When needed, the film adhesive is removed from the low temperature environment and applied to a metal or composite part, the backing is stripped off and the assembly completed and cured in an oven or autoclave.

The following examples are illustrative of the present invention and are not intended to limit the scope of the invention in any way.

EXAMPLES

The following materials were employed in the Examples:
D.E.R.™ 331™ Liquid Epoxy Resin: a liquid reaction product of epichlorohydrin and bisphenol A available from The Dow Chemical Company
HMDA: Hexamethylenediamine available from Sigma Aldrich
IPDA: Isophorone diamine available from Sigma Aldrich
PETMP: Pentaerythritol tetrakis(3-mercaptopropionate) available from Bruno Bock Chemische Fabrik GmbH & Co. KG TMPMP: Trimethylolpropane tris(3-mercaptopropionate) available from Bruno Bock Chemische Fabrik GmbH & Co. KG JEFFAMINE ED-600: Aliphatic polyether diamine derived from a propylene oxide-capped polyethylene glycol, available from Huntsman Corporation PRIAMINE® 1074: Dimer diamine available from Croda Coatings & Polymers DBU: 1,8-Diazabicyclo[5.4.0]undec-7-ene, available from Acros Organics WPBG-266: 1,2-Diisopropyl-3-[Bis(dimethylamino)methylene] guanidium 2-(3-benzoylphenyl) propionate, available from Fujifilm Wako Pure Chemical Corporation.

Example 1

EtOMAL ($R^a$=Et, 0.50 g, 3.2 mmol) was dissolved in dichloromethane (5.0 ml). HMDA (0.38 g, 3.2 mmol) was added to the solution and the reaction mixture was then stirred at room temperature for 5 hours. A dark brown polymer was obtained after solvent evaporation. The obtained polymer was analyzed by Differential Scanning calorimetry (DSC) from −50 to 200° C. with a heating rate of 10 K/min: as noted in Table 1 herein below, the glass transition temperature ($T_g$) of the polymer was determined as 43.4° C. (Table 1, Entry 1). $^1$H NMR spectroscopy and Gel Permeation Chromatography (GPC) analysis revealed that EtOMAL undergoes nucleophilic addition with amine twice to form a polymer having aminal bonds in its backbone, as illustrated in Scheme 1 below.

Scheme 1. Reaction of EtOMAL with HMDA.

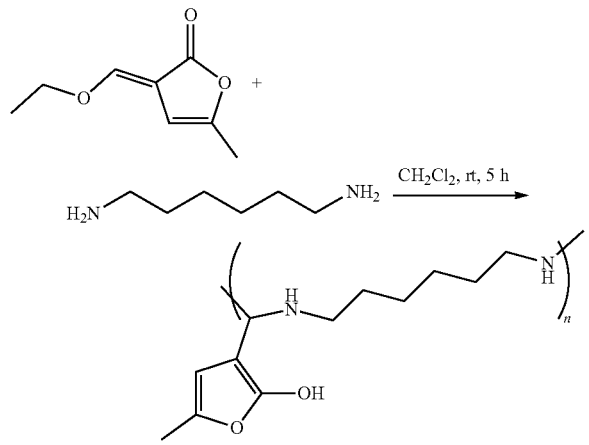

$^1$H NMR (400 MHz, DMSO-$d_6$) δ 7.12 (s, 1H), 5.98 (s, 1H), 3.31-3.24 (m, 4H), 1.99 (s, 3H), 1.58-1.42 (br, 4H), 1.41-1.19 (br, 6H). GPC (THF) $M_w$=75,000, $M_w/M_n$=2.4.

Example 2

EtOMAL ($R^a$=Et, 0.01 g) and Jeffamine ED-600 (0.03 g) were separately placed on an aluminum sample dish (Diameter: 4 mm). The sample dish was immediately cooled to −50° C. and then heated at a rate of 10 K/min employing Differential Scanning calorimetry (DSC) to follow the reaction.

As illustrated in FIG. 1 appended hereto, melting of EtOMAL was detected as an endothermic peak at 34.3° C. An exothermic peak at 47.0° C. was observed which was rationalized as the melted EtOMAL reacting with Jeffamine ED-600 to be cured. As further indicated in FIG. 1, the obtained resin did not show any clear glass transition and crystallization on DSC in the range from −50 to 200° C. on account of its amorphous nature.

Example 3: Curing of XOMAL with Multifunctional Amines

The following typifies the procedure employed in this Example for the curing of XOMAL with a multifunctional amine.

EtOMAL ($R^a$=Et) and IPDA (multifunctional amine) were mixed at the molar ratio EtOMAL:IPDA of 1:1. The mixture was maintained at room temperature for 24 hours. The obtained dark brown polymer was analyzed by Differential Scanning calorimetry (DSC) in the temperature range from −50 to 200° C. at a heating rate of 10 K/min: the determined glass transition temperature ($T_g$) was 70.0° C. (Table 1, Entry 2).

This procedure was repeated for the reactants identified in Table 1 below, the molar amounts of each reactant being indicated in brackets. The theoretical bio-renewable carbon content of the compositions given in Table 1 was calculated based on the values applied to the following ingredients: EtOMAL (63% bio-renewable); Priamine 1074 (100% bio-renewable); and, all other components (0% bio-renewable).

TABLE 1

| Entry | XOMAL | Epoxy | Hardener | Catalyst | Theoretical bio-renewable content (%) | $T_g$ (° C.) |
|---|---|---|---|---|---|---|
| 1 | EtOMAL (1.0) | | HMDA (0.75) | | 36.3 | 43.4 |
| 2 | EtOMAL (1.0) | | IPDA (1.1) | | 30.2 | 70.0 |
| 3 | EtOMAL (1.0) | | Jeffamine ED-600 (3.9) | | 13.0 | <−50 |
| 4 | EtOMAL (1.0) | | Priamine 1074 (3.5) | | 91.9 | 22.7 |
| 5 | EtOMAL (1.0) | | IPDA (0.55), Priamine 1074 (1.7) | | 72.2 | −7.2 |
| 6 | EtOMAL (1.0) | DER 331 (2.4) | HMDA (1.5) | | 12.9 | 46.0 |
| 7 | EtOMAL (1.0) | DER 331 (2.4) | IPDA (2.2) | | 11.3 | 75.6 |
| 8 | EtOMAL (1.0) | DER 331 (1.2) | IPDA (1.7) | | 16.4 | 73.8 |
| 9 | | DER 331 (5.0) | IPDA (2.3) | | 0.0 | 80.6 |
| 10 | EtOMAL (1.0) | | PETMP (1.6) | DBU (0.26) | 22.4 | 46.9 |
| 11 | EtOMAL (1.0) | | TMPMP (1.7) | DBU (0.27) | 21.2 | 7.7 |

TABLE 1-continued

| Entry | XOMAL | Epoxy | Hardener | Catalyst | Theoretical bio-renewable content (%) | $T_g$ (° C.) |
|---|---|---|---|---|---|---|
| 12 | | DER 331 (5.0) | PETMP (3.3) | DBU (0.83) | 0.0 | 38.7 |
| 13 | | DER 331 (5.0) | TMPMP (3.6) | DBU (0.86)) | 0.0 | 34.9 |
| 14 | EtOMAL (1.0) | | PETMP (1.6) | WPBG-266 (0.13) | 23.4 | 22.6 |
| 15 | EtOMAL (1.0) | | TMPMP (1.7) | WPBG-266 (0.14) | 22.3 | -2.8 |

As demonstrated in Entries 1 to 5 of Table 1, the glass transition temperatures ($T_g$) of the obtained polymers are tunable through the selection and/or mixing of amine hardeners. Theoretical bio-renewable content is improved by using EtOMAL as compared to the petroleum-based epoxy DER331 and can reach up to 92% by choosing the bio-renewable diamine, Priamine 1074 (Table 1, Entry 4).

Entries 6 to 8 in Table 1 further demonstrate that EtOMAL is co-polymerizable with the commonly used epoxy DER331. These facts evidence that one may provide a curable composition of XOMAL with multifunctional amines and also use XOMAL as a reactive component in epoxy-based adhesives/thermosets in order to improve the carbon footprint thereof.

Example 4: Curing of XOMAL with Multifunctional Thiols 4.1 Thermal Curing

A multifunctional thiol PETMP (0.16 g, 0.32 mmol) was mixed with a base catalyst DBU (0.026 g, 0.17 mmol). Upon addition of EtOMAL ($R^a$=Et, 0.1 g, 0.65 mmol) to the mixture at room temperature, curing took place simultaneously to form a light yellow resin. The obtained resin was analyzed on Differential Scanning calorimetry (DSC) from −50 to 200° C. with heating rate at 10 K/min: the glass transition temperature ($T_g$) was detected at 46.9° C. The detected $T_g$ was listed in Table 1 along with theoretical bio-renewable carbon content.

4.2 Photo-Curing

EtOMAL ($R^a$=Et, 0.15 g, 0.97 mmol), a multifunctional thiol PETMP (0.24 g, 0.49 mmol), and a photo-base generator WPBG-266 (0.019 g, 0.038 mmol) were mixed and placed on a Teflon plate. The mixture was exposure to UV light irradiation for 5 min and then left at room temperature to obtain a light yellow resin. The obtained resin was analyzed on Differential Scanning calorimetry (DSC) from −50 to 200° C. with heating rate at 10 K/m in to detect $T_g$ at 22.6° C. The detected $T_g$ was listed in Table 1 along with theoretical bio-renewable carbon content.

The present results clearly demonstrate that XOMAL is curable with commonly used thiol hardeners in the presence of base catalyst and improves carbon footprint as compared to petroleum-based epoxy DER331. By choosing base catalysis, the curing may be thermally and photo-chemically initiated.

Example 5: Preparation of Cured Resin of Epoxy with XOMAL and its Degradation The generalized procedure was followed to prepare a cured epoxy resin with XOMAL and to monitor its degradation.

EtOMAL ($R^a$=Et, 0.3 g) was mixed with a conventional epoxy monomer DER331 (3.0 g) and then IPDA (0.85 g) was added as a hardener. The prepared mixture was heated at 80° C. for 4 hours and subsequently at 150° C. for 2 hours to obtain a stiff resin ($T_g$=139° C.).

As a comparison, DER331 (3.0 g) was cured with IPDA (0.70 g) in the absence of EtOMAL under the identical conditions to obtain a stiff resin ($T_g$=151° C.).

The cured resins (ca. 1 cm×2 cm×2 mm) were immersed in an acidic solution ($H_2O$:$CH_3COOH$=1:1 (v/v)) for 48 hours at room temperature. The cured epoxy resin without EtOMAL was intact after the immersion for 2 days under the present conditions. In sharp contrast, the cured epoxy resin with EtOMAL was degraded into small pieces (<ca. 1 mm×1 mm×1 mm) under the identical conditions.

The results demonstrated that EtOMAL is co-cured with epoxy by amine hardener to form aminal bonds and the cured resin is degraded by acid-catalyzed hydrolysis of aminal. Consequently, XOMAL may be used as a component in epoxy-based adhesives/thermosets to improve the carbon footprint thereof and may also provide a degradable composition to debond/disassemble those adhesives/thermosets for the purposes of recycling.

In view of the foregoing description and examples, it will be apparent to those skilled in the art that equivalent modifications thereof can be made without departing from the scope of the claims.

What is claimed is:

1. A reactive composition comprising:
   a) a functionalized α-angelica lactone (XOMAL) having the general formula

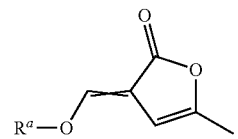

wherein $R^a$ is a $C_1$-$C_{30}$ alkyl, $C_3$-$C_{30}$ cycloalkyl, $C_6$-$C_{18}$ aryl or $C_2$-$C_{12}$ alkenyl group; and
   b) a curative component comprising at least one of i) and ii):
      i) at least one polyamine having at least two amine hydrogens reactive toward epoxide groups; and
      ii) at least one mercapto compound having at least two mercapto groups reactive toward epoxide groups.

2. The composition according to claim 1, wherein said functionalized α-angelica lactone (XOMAL) a) has the general formula:

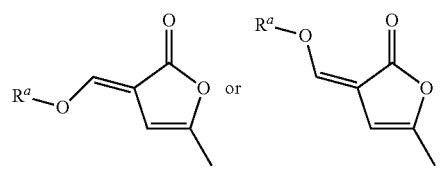

wherein: $R^a$ is a $C_1$-$C_{18}$ alkyl, $C_3$-$C_{18}$ cycloalkyl, $C_6$-$C_{18}$ aryl or $C_2$-$C_{10}$ alkenyl group.

3. The composition according to claim 1, wherein substituent $R^a$ of said functionalized α-angelica lactone (XOMAL) a) is a $C_1$-$C_{12}$ alkyl or $C_2$-$C_8$ alkenyl group.

4. The composition according to claim 1, wherein substituent $R^a$ of said functionalized α-angelica lactone (XOMAL) a) is a $C_1$-$C_4$ alkyl or $C_2$-$C_4$ alkenyl group.

5. The composition according to claim 1, wherein said at least one polyamine b) i) contains primary and/or secondary amine groups and has an equivalent weight per said amine groups of not more than 150.

6. The composition according to claim 1, wherein said at least one polyamine b) i) comprises an aliphatic amine selected from the group consisting of: isophorone diamine (IPDA); hexamethylene diamine (HMDA); 1,3-bis(aminomethyl)cyclohexane; 1,4-bis(aminomethyl)cyclohexane; bis(4-amino-cyclohexyl)methane; bis(4-amino-3-methylcyclohexyl)methane; 2,5(2,6)-bis(aminomethyl)-bicyclo[2.2.1]heptane (NBDA); and ether group-containing polyamines with an average molecular weight of up to 2000 g/mol.

7. The composition according to claim 1, wherein said at least one mercapto compound b) ii) is selected from polyesters of thiocarboxylic acids and mixtures of said polyesters.

8. The composition according to claim 7, wherein said at least one mercapto compound b) ii) is selected from the group consisting of pentaerythritol tetramercapto-acetate (PETMP), trimethylolpropane trimercaptoacetate (TMPMP), glycol dimercaptoacetate and mixtures thereof.

9. A curable composition comprising the reactive composition as defined in claim 1 and c) at least one epoxide compound.

10. The curable composition according to claim 9, wherein said at least one epoxide compound c) is a polyepoxide selected from the group consisting of: glycidyl ethers of polyhydric alcohols, glycidyl ethers of polyhydric phenols, glycidyl esters of polycarboxylic acids, epoxidized polyethylenically unsaturated hydrocarbons, epoxidized esters, epoxidized ethers, and epoxidized amides.

11. The curable composition according to claim 9, characterized by a molar ratio of epoxy-reactive groups to epoxy groups from 0.95:1 to 1.5:1.

12. The curable composition according to claim 9, comprising, based on the weight of the composition: from 10 to 40 wt. % of a); from 20 to 50 wt. % of b); and from 10 to 50 wt. % of c).

13. The curable composition according to claim 12, wherein:
$R^a$ of said functionalized α-angelica lactone (XOMAL) a) is a $C_1$-$C_4$ alkyl or $C_2$-$C_4$ alkenyl group;
said at least one polyamine b) i)
contains primary and/or secondary amine groups and has an equivalent weight per said amine groups of not more than 150;
said at least one mercapto compound b) ii) is
selected from the group consisting of pentaerythritol tetramercapto-acetate (PETMP), trimethylolpropane trimercaptoacetate (TMPMP), glycol dimercaptoacetate and mixtures thereof; and
said at least one epoxide compound c) is
selected from the group consisting of: glycidyl ethers of polyhydric alcohols, glycidyl ethers of polyhydric phenols, and glycidyl esters of polycarboxylic acids.

14. A cured product obtained by curing the composition as defined in claim 9.

* * * * *